US011999968B2

(12) United States Patent
Lee et al.

(10) Patent No.: US 11,999,968 B2
(45) Date of Patent: Jun. 4, 2024

(54) MODIFIED T CELLS, PHARMACEUTICAL COMPOSITION, MANUFACTURING METHOD THEREOF, AND METHOD OF USING THE SAME

(71) Applicant: FullHope Biomedical Co., Ltd, New Taipei (TW)

(72) Inventors: Jan-Mou Lee, New Tapei (TW); Chun-Wei Yu, New Tapei (TW); Chih-Hao Fang, New Tapei (TW); Ya-Fang Cheng, New Tapei (TW); Li-Tzong Chen, Kaohsiung (TW)

(73) Assignee: FullHope Biomedical Co., Ltd, New Taipei (TW)

( * ) Notice: Subject to any disclaimer, the term of this patent is extended or adjusted under 35 U.S.C. 154(b) by 90 days.

(21) Appl. No.: 17/508,446

(22) Filed: Oct. 22, 2021

(65) Prior Publication Data
US 2023/0131917 A1    Apr. 27, 2023

(51) Int. Cl.
*C12N 5/0783* (2010.01)
*A61K 35/17* (2015.01)
*C07K 14/54* (2006.01)
*C07K 14/55* (2006.01)

(52) U.S. Cl.
CPC ............ *C12N 5/0636* (2013.01); *A61K 35/17* (2013.01); *C07K 14/5434* (2013.01); *C07K 14/55* (2013.01)

(58) Field of Classification Search
None
See application file for complete search history.

(56) References Cited

U.S. PATENT DOCUMENTS

2019/0119634 A1* 4/2019 Jakobovits .............. A61P 31/00

FOREIGN PATENT DOCUMENTS

CN    110184240 B    11/2020
WO    WO2016087871    6/2016

OTHER PUBLICATIONS

Johnson, M. Fetal Bovine Serum. Mater Methods Mar. 22, 2012;2:117. dx.doi.org/10.13070/mm.en.2.117. (Year: 2012).*
Guiotto M, Raffoul W, Hart AM, Riehle MO, di Summa PG. Human platelet lysate to substitute fetal bovine serum in hMSC expansion for translational applications: a systematic review. J Transl Med. Sep. 15, 2020;18(1):351. doi: 10.1186/s12967-020-02489-4. PMID: 32933520; PMCID: PMC7493356. (Year: 2020).*
Peters Christian et al: "TGF-[beta] enhances the cytotoxic activity of V[delta]2 T cells", Oncoimmunology, vol. 8, No. 1, Sep. 26, 2018 (Sep. 26, 2018), XP093028090, DOI: 10.1080/2162402X.2018. 1522471CC=XP; XP093028090 (Cat. X,Y).
Domae Eisuke et al: "Synergistic effect of IL-2, IL-12 and IL-18 on the activation of ex vivo-expanded human V [gamma]9V[delta]2 T cells", J Osaka Dent Univ, Apr. 1, 2018 (Apr. 1, 2018), pp. 51-57, XP093029886, Retrieved from the Internet <URL:https://www. jstage.jst.go.jp/article/jodu/52/1/52_51/_pdf/-char/ja> [retrieved on Mar. 8, 2023]CC=XP; XP093029886 (Cat. X).
Izumi Takamichi et al: "Ex vivo characterization of [gamma][delta] T-cell repertoire in patients after adoptive transfer of V[gamma]9V[delta]2 T cells expressing the interleukin-2 receptor [beta]-chain and the common [gamma]-chain", Cytotherapy, vol. 15, No. 4, Apr. 1, 2013 (Apr. 1, 2013), GB, pp. 481-491, XP093029843, ISSN: 1465-3249, DOI: 10.1016/j.jcyt.2012.12.004CC=XP; XP093029843 (Cat. Y).
Kakimi Kazuhiro et al: "[gamma][delta] T Cell Therapy for the Treatment of Non-small Cell Lung Cancer", Translational Lung Cancer Research, Feb. 1, 2014 (Feb. 1, 2014), China, pp. 23-33, XP093029845, Retrieved from the Internet URL:https://tlcr.amegroups. com/article/view/1803/2724> [retrieved on Mar. 8, 2023], DOI: 10.3978/j.issn.2218-6751.2013.11.01CC=XP; XP093029845 (Cat. Y).
Beatson Richard E. et al: "TGF-[beta]1 potentiates V[gamma]9V[delta]2 T cell adoptive immunotherapy of cancer", Cell Reports Medicine, vol. 2, No. 12, Dec. 1, 2021 (Dec. 1, 2021), pp. 100473, XP093028083, ISSN: 2666-3791, DOI: 10.1016/j.xcrm.2021.100473CC=XP; XP093028083 (Cat. X,P).
Qualai, Jamal, et al. Expression of CD11c is associated with unconventional activated T cell subsets with high migratory potential. PloS one, 2016, 11.4: e0154253.
Tsuda, Junko, et al. Involvement of CD56brightCD11c+ Cells in IL-18-Mediated Expansion of Human γδ T Cells. The Journal of Immunology, 2011, 186.4: 2003-2012.
Silva, Polyana Barbosa, et al. Immunological Characteristics between αβ T DC and γδ T DC Cells in the Spleen of Breast Cancer-Induced Mice. Revista Brasileira de Ginecologia e Obstetrícia, 2021, 43: 368-373.
Glatzel, Andrea, et al. Patterns of chemokine receptor expression on peripheral blood γδ T lymphocytes: strong expression of CCR5 is a selective feature of Vδ2/Vγ9 γδ T cells. The Journal of Immunology, 2002, 168.10: 4920-4929.
Dagna, Lorenzo, et al. Skewing of cytotoxic activity and chemokine production, but not of chemokine receptor expression, in human type-1/-2 γ δ T lymphocytes. European journal of immunology, 2002, 32.10: 2934-2943.
Poggi, Alessandro, et al. Migration of Vδ1 and Vδ2 T cells in response to CXCR3 and CXCR4 ligands in healthy donors and HIV-1-infected patients: competition by HIV-1 Tat. Blood, 2004, 103.6: 2205-2213.

* cited by examiner

*Primary Examiner* — Allison M Fox
*Assistant Examiner* — Alyssa G Weston
(74) *Attorney, Agent, or Firm* — Branch Partners PLLC; Bruce E. Black

(57) ABSTRACT

This disclosure provides modified T cells possessing both cell killing function and antigen presenting cell function and method of culturing the same. By administration of the modified T cell, cancer cells in a subject may be effectively inhibited via cell-mediated immunity.

9 Claims, 23 Drawing Sheets

IL-2+IL-12
+day12 IL-18 15 ng/mL

Net MFI= 3.35

IL-2+IL-12
+day12 IL-18 45 ng/mL

Net MFI= 3.92

IL-2+IL-12
+day12 IL-18 15 ng/mL

IL-2+IL-12
+day12 IL-18 45 ng/mL

```
┌─────────────────────────────────────────────┐
│   Obtaining a body fluid comprising mononuclear │
│                    cells                    │
└─────────────────────────────────────────────┘
                      │
                      ▼
┌─────────────────────────────────────────────┐
│   Contacting the mononuclear cells with an  │
│  inducing culturing medium comprising IL-2 and │
│    zoledronic acid to obtain a first cultured cell │
│                 population                  │
└─────────────────────────────────────────────┘
                      │
                      ▼
┌─────────────────────────────────────────────┐
│ Contacting the first cultured cell population with │
│    a first culturing medium comprising IL-2to │
│     obtain a second cultured cell population │
└─────────────────────────────────────────────┘
                      │
                      ▼
┌─────────────────────────────────────────────┐
│  Contacting the second cultured cell population │
│  with a second culturing medium comprising IL-2 │
│    and IL-12 to obtain a third cultured cell │
│                 population                  │
└─────────────────────────────────────────────┘
```

FIG. 11

MODIFIED T CELLS, PHARMACEUTICAL COMPOSITION, MANUFACTURING METHOD THEREOF, AND METHOD OF USING THE SAME

FIELD OF INVENTION

The disclosure relates to modified T cells, particularly γδ T cells, and pharmaceutical compositions comprising the same. Methods are also provided for identifying the modified T cells and culturing of the modified T cells.

BACKGROUND OF THE INVENTION

Immune surveillance plays a critical role against cancer and represents a very attractive therapeutic approach, especially in light of the many shortcomings of conventional surgery, radiation and chemotherapies in the management of cancer.

Gamma delta (γδ) T cells are the prototype of "unconventional" T cells and represent a relatively small subset of T cells in peripheral blood. They are defined by expression of heterodimeric T-cell receptors (TCRs) composed of γ and δ chains. This sets them apart from the classical and much better known CD4$^+$ helper T cells and CD8$^+$ cytotoxic T cells that express αβ TCRs.

Vγ9Vδ2 (also termed Vγ2Vδ2) T cells are a human peripheral blood γδ T cell subset recognizing microbial (E)-4-hydroxy-3-methylbut-2-enyl diphosphate and endogenous isopentenyl diphosphate in a TCR-dependent manner. The recognition does not require specific accessory cells, antigen uptake, antigen processing, or MHC class I, class II, or class Ib expression.

γδ T cells are considered to represent a link between innate and adaptive immunity. They express natural killer receptors, such as NKG2D, which makes important contributions to the tumor reactivity of Vγ9Vβ2) T cells. In addition, they also express γδ T cell receptors. Activated γδ T cells express a high level of antigen-presenting cell-related molecules and can present peptide antigens derived from destructed cells to αβ T cells. Utilizing these antimicrobial and anti-tumor properties of γδ T cells, preclinical and clinical trials have been conducted to develop novel immunotherapies for infections and malignancies.

These findings support a rationale for develop a T cell based therapy against cancer cells and culture methods to generate greater number of therapeutically competent T cells for clinical applications, as there is still an unmet need for effective treatment and/or prevention for cancer. The present disclosure provides modified T cells having a unique phenotype to satisfy these and other needs. The cells can be used in autologous therapy or in non-autologous therapy.

SUMMARY OF THE INVENTION

In view of the urgent need of the art, provided herein are modified T cells and pharmaceutical compositions comprising the same that are safe and effective in the treatment of the cancer.

In one embodiment, the present disclosure provides a modified T cell comprising a phenotype of CD3$^{Hi}$TCR γ9$^{Hi}$TCR δ2$^{Hi}$CXCR4$^{Hi}$. In a preferred embodiment, the modified T cell may further comprise a phenotype of CD69$^{Dim}$CD11c$^{Hi}$CXCR3$^{Dim}$, i.e. the modified T cell may comprise a phenotype of CD3$^{Hi}$TCR γ9$^{Hi}$TCR δ2$^{Hi}$CD69$^{Dim}$ CD11c$^{Hi}$CXCR4$^{Hi}$CXCR3$^{Dim}$. In another preferred embodiment, the modified T cell may further comprise a phenotype of IFN-γ$^{Hi}$.

Some embodiments provide pharmaceutical compositions comprising a modified γδ T cell described herein and a pharmaceutically acceptable carrier or excipient.

Some embodiments provide a method of treating cancer cells, comprising administering an effective amount of modified T cells or pharmaceutical compositions as described herein to a subject in need thereof.

In a preferred embodiment, the effective amount may be about 1×10$^3$ to about 1×10$^9$ cells per dose.

In a preferred embodiment, the modified T cell may be autologous or allogeneic.

In a preferred embodiment, the modified T cell may be derived from peripheral blood, cord blood or bone marrow.

In a preferred embodiment, the method may further comprise expanding the modified T cell in vitro.

Other embodiments provide a method of culturing a modified T cell possessing both NK cell function and antigen-presenting cell function, comprising
  obtaining a body fluid comprising mononuclear cells;
  contacting the mononuclear cells with an inducing culturing medium comprising IL-2 and zoledronic acid to obtain a first cultured cell population;
  contacting the first cultured cell population with a first culturing medium comprising IL-2 to obtain a second cultured cell population; and
  contacting the second cultured cell population with a second culturing medium comprising IL-2 and IL-12 to obtain a third cultured cell population.

In a preferred embodiment, the mononuclear cells may be derived from peripheral blood, cord blood or bone marrow.

In a preferred embodiment, the inducing medium, the first culturing medium and the second culturing medium may further comprise a hematopoietic cell medium, preferably an AIM-V medium.

In a preferred embodiment, the inducing medium, the first culturing medium and the second culturing medium may further comprise a serum protein, preferably a human platelet lysate.

In a preferred embodiment, the mononuclear cells may be in contact with the inducing culturing medium for about 1-3 day(s).

In a preferred embodiment, the first cultured cell population may be in contact with the first culturing medium for about 1-6 day(s).

In a preferred embodiment, the second cultured cell population may be in contact with the second culturing medium for about 1-3 day(s).

In a preferred embodiment, the method may further comprise contacting the third cultured cell population with a third culturing medium comprising IL-2, IL-12 and IL-18 after contacting with the second culturing medium to obtain a fourth cultured cell population.

In a preferred embodiment, the third culturing medium may further comprise a hematopoietic cell medium, preferably an AIM-V medium.

In a preferred embodiment, the third culturing medium may further comprise a serum protein, preferably a human platelet lysate.

In a preferred embodiment, the third cultured cell population may be in contact with the third culturing medium for about 1-3 day(s).

In a preferred embodiment, the method may further comprise isolating a modified T cell with a phenotype of CD3$^{Hi}$TCR γ9$^{Hi}$TCR δ2$^{Hi}$CXCR4$^{Hi}$.

The culturing methods described herein allow for isolation of a greater number of modified T cells from a fixed amount of a sample, for example, 10 mL of blood.

BRIEF DESCRIPTION OF THE DRAWINGS

Illustrative embodiments of the present application are described in detail below with reference to the following figures:

FIG. 11 is a flow chart in accordance with an embodiment of the method of culturing a modified T cell.

DETAILED DESCRIPTION

Figure 1:
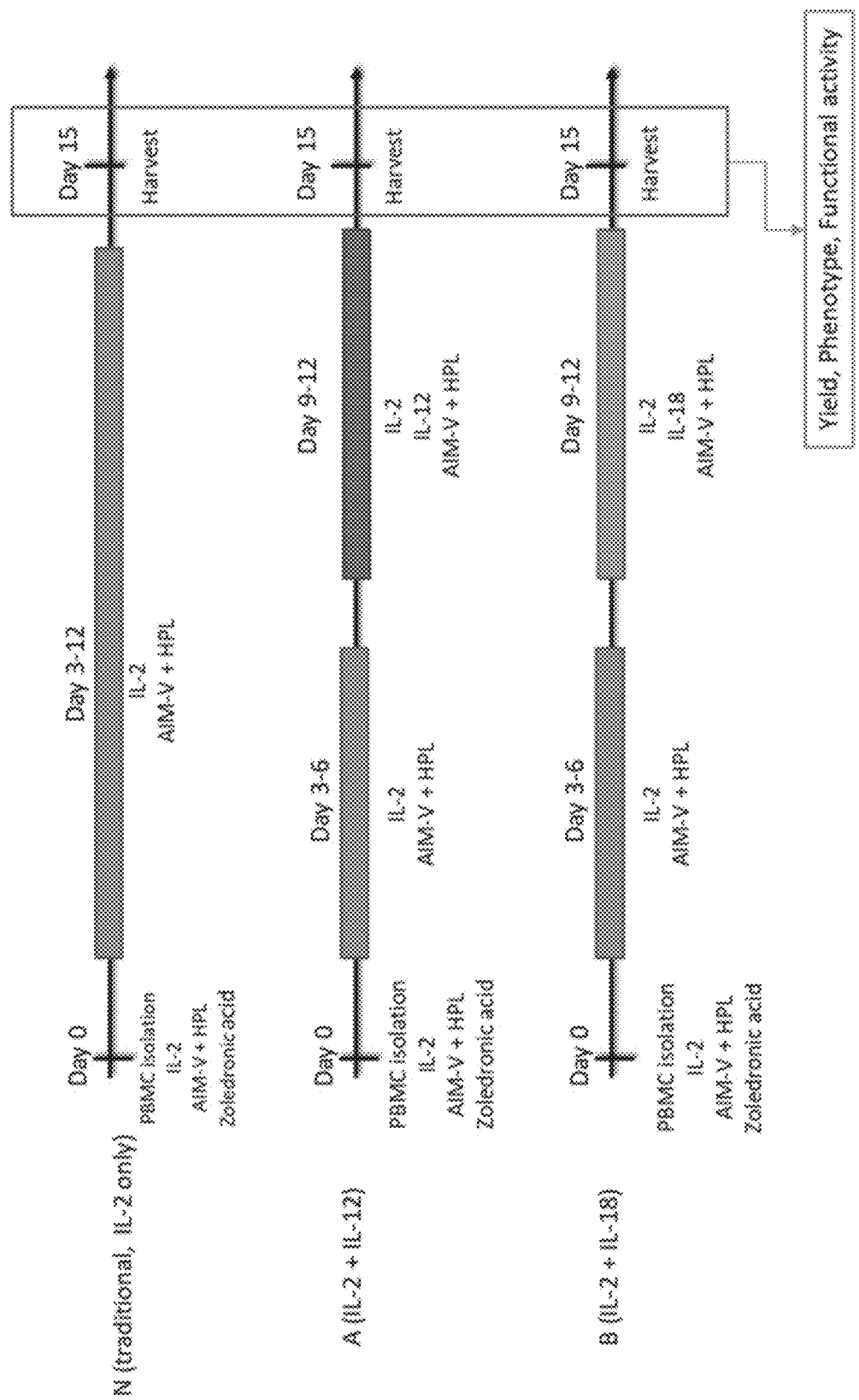
FIG. 1 illustrates the experimental design to determine which cytokine cocktail play major role in phenotype and functional development.

The foregoing and other aspects of the present disclosure will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any elements, steps, or ingredients not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Where applicants have defined an invention or a portion thereof with an open-ended term such as "comprising," it should be readily understood that (unless otherwise stated) the description should be interpreted to also describe such an invention using the term "consisting of."

All numbers herein may be understood as modified by "about." As used herein, the term "about" is used to indicate that a value includes for example, the inherent variation of error for a measuring device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

"Subject" as used herein refers to animals, including, for example, a mammalian subject diagnosed with or suspected of having or developing cancer(s). In an embodiment, the term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, apes, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

"Administering" or "Administration" is referred to herein as providing a modified T cell or a pharmaceutical composition of the present application to a subject. By way of example and not limitation, administration may be performed via parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal. For example, injection may be performed by intravenous (i.v.) injection, subcutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route.

The use of the terms "treating," or "treatment" is referred to herein as administration of a T cell or a pharmaceutical composition to a subject with the purpose to cure, alleviate, relieve, remedy, prevent, or ameliorate a disorder, symptoms of the disorder, a disease state secondary to the disorder, or predisposition toward the disorder. The terms "inhibiting," "reducing," or "prevention," or any variation of these terms, when used in the claims and/or the specification includes any measurable decrease or complete inhibition to achieve a desired result.

"Cancer(s)" that may be treated by the T cell or the pharmaceutical composition of the application include those classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); lymphomas (Hodgkin's disease and non-Hodgkin's lymphoma), multiple myeloma, and leukemias (lymphocytic leukemia; myeloid leukemia; monocytic leukemia; and other leukemias).

Other cancers, classified by histological type, that may be suitable targets for the therapeutic compositions according to the present application include, but are not limited to, neoplasm, malignant; Carcinoma, not otherwise specified (NOS); Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Bronchioloalveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extramammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

An "effective amount," as used herein, refers to a dose of the modified T cells or pharmaceutical composition that is sufficient to reduce the symptoms and signs of cancer, which include, but are not limited to, weight loss, pain or tumor mass which is detectable, either clinically as a palpable mass or radiologically through various imaging means.

In certain embodiments, it is desired to limit, reduce, or ameliorate the size of tumor or cancer lesions. The routes of administration will vary, naturally, with the location and nature of the lesion or site to be targeted, and include, e.g., regional, parenteral, intravenous, intramuscular, and/or systemic administration and formulation. Direct injection or injection into the vasculature or the vessels to and from and within an organ or tissue is specifically contemplated for target areas. Local, regional, or systemic administration also may be appropriate.

In the disclosure herein, the expression level or surface density of the cell surface antigen using FACS/flow cytometry analysis are defined in Table 1. The interpretation for the various expression levels in Table 1 is an example of defining the expression level of the cell surface antigen. It should be noted that the flow cytometry signal level intensity varies with the following factors: the flow cytometry, the software and different batches of antibody used.

TABLE 1

| Symbol | Interpretation |
| --- | --- |
| − | Net mean fluorescence intensity (MFI) ≤ 0 |
| + | 0 < net MFI |
| + (Low) | 0 < net MFI ≤ 0.1 |
| + (Dim) | 0.1 < net MFI ≤ 2 |
| + (Hi) | 2 < net MFI |

Unless otherwise defined, all technical and scientific terms used herein have the same meaning as commonly understood by one of ordinary skill in the art to which this invention belongs. All publications, patent applications, patents and other references cited herein are incorporated by reference in their entireties for the teachings relevant to the sentence and/or paragraph in which the reference is presented.

Modified T Cells

Naturally occurring or conventional T cells have $CD3^{Hi}TCR\ \gamma9^{Hi}TCR\ \delta2^{Hi}$ phenotype. In one embodiment, the naturally occurring or conventional T cells have $CD3^{Hi}TCR\ \gamma9^{Hi}TCR\ \delta2^{Hi}CXCR4^{Dim}CXCR3^{Hi}$ phenotype, as illustrated in Table 2.

In one embodiment, the present application provides a modified T cell comprising a $CD3^{Hi}TCR\ \gamma9^{Hi}TCR\ \delta2^{Hi}CXCR4H$ cell phenotype, as illustrated in Table 2. Preferably, the modified T cell may further comprise a phenotype of $CD69^{Dim}CD11c^{Hi}CXCR3^{Dim}$. Preferably, the modified T cell may further comprise a phenotype of $IFN-\gamma^{Hi}$. The modified T cell of the present application is non-naturally occurring. The modified T cells possess both cell-killing function and antigen-presenting function and an enhanced anti-cancer activity.

TABLE 2

Phenotypic comparison of conventional T cells and modified T cells

|  | Conventional T | Modified T |
| --- | --- | --- |
| CD3 | + (Hi) | + (Hi) |
| TCR γ9 | + (Hi) | + (Hi) |
| TCR δ2 | + (Hi) | + (Hi) |
| CD69 | + (Low) | + (Dim) |
| CD11c | + (Low) | + (Hi) |
| CXCR4 | + (Dim) | + (Hi) |
| CXCR3 | + (Hi) | + (Dim) |
| IFN-γ | − | + (Hi) |

Chemokine receptors are best known for their ability to stimulate the migration of cells. Immune cell recruited into the tumor by chemokine-chemokine receptor interactions. Among the chemokine receptors, CXCR4 is required for normal accumulation of plasma cells in the bone marrow and critically important for homing of all CD8 T-cell subsets to the BM in mice. According to previous study, Vδ2 T cells are $CXCR3^{Hi}CXCR4^{Dim}$, while Vδ1 are mostly $CXCR4^+$.

In one embodiment, the expression level or surface density of the cell surface antigen is quantified by exposing the modified T cells to a fluorescent dye-tagged specific anti-human monoclonal antibody (e.g., CD86-PE (Beckman Coulter; Cat. No: IM2729U)), followed by sorting of the modified T cells using flow cytometer (e.g. Navios, commercially available from Beckman Coulter, Inc., USA).

The modified T cells can be generated from a single individual, e.g. autologous or allogeneic.

Pharmaceutical Composition

In one embodiment, the present application provides pharmaceutical compositions comprising a modified T cell described herein, and a pharmaceutically acceptable carrier or excipient.

The present application also provides methods of inhibiting cancer cells by administering to a subject in need thereof the present modified T cells or the present pharmaceutical composition in an amount effective to inhibit cancer cells. Without being bound by any particular theory, it is believed that the modified T cells inhibit cancer cells by one or more of the T cell/antigen-presenting cell functions: enhancing cytotoxicity and stimulating cancer-specific T lymphocyte proliferation.

Routes of administration of the present pharmaceutical compositions or modified T cells include, but are not limited to, intravenous, intramuscular, subcutaneous, oral, topical, intradermal, transdermal, subdermal, parenteral, rectal, spinal, or epidermal administration. In one embodiment, the modified T cells are administered by intravenous injection or infusion.

The pharmaceutical compositions of the present application can be prepared as injectables, either as liquid solutions or suspensions, or as solid forms which are suitable for solution or suspension in liquid vehicles prior to injection.

The present modified T cells are formulated into pharmaceutical compositions for delivery to a mammalian subject. The pharmaceutical composition is administered alone, and/or mixed with a pharmaceutically acceptable vehicle, excipient or carrier. Suitable vehicles are, for example, saline (e.g. normal saline), dextrose, glycerol, platelet-rich plasma (PRP), or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the present application. Physiologically acceptable compounds can include, e.g., carbohydrates, such as glucose, sucrose, or dextran, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present application can also include ancillary substances, such as pharmacological agents, cytokines, or other biological response modifiers.

Actual methods of preparing such dosage forms are known, or will be apparent, to those skilled in the art. See, e.g., Remington's Pharmaceutical Sciences, Mack Publishing Company, Easton, Pennsylvania, 21st edition.

The modified T cells or the present pharmaceutical compositions can be administered in a single dose treatment or in multiple dose treatments on a schedule and over a time period appropriate to the age, weight and condition of the subject, the particular composition used, and the route of administration, whether the modified T cells or the present pharmaceutical composition is used for prophylactic or curative purposes, etc. For example, in one embodiment, the modified T cells or pharmaceutical composition according to the present application is administered once per month, twice per month, three times per month, every other week (qow), once per week (qw), twice per week (biw), three times per week (tiw), four times per week (qiw), five times per week, six times per week, every other day (qod), daily (qd), twice a day (bid), three times a day (tid) or four times a day (qid).

The duration of treatment of the modified T cells or the pharmaceutical composition according to the present application, e.g., the period of time over which the modified T cell or pharmaceutical composition is administered, can vary, depending on any of a variety of factors, e.g., subject response, etc. For example, the modified T cells or pharmaceutical composition can be administered over a period of time ranging from about one or more seconds to one or more minutes, one or more hours to one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

It is advantageous to formulate parenteral pharmaceutical compositions or modified T cells in dosage unit form for ease of administration and uniformity of dosage. Dosage unit form as used herein refers to physically discrete units suited as unitary dosages for the subject to be treated; each unit containing a predetermined quantity of modified T cells calculated to produce the desired therapeutic effect in association with the required pharmaceutical carrier.

The data obtained from the cell culture assays and animal studies can be used in formulating a range of dosage for use in humans. In one embodiment, the dosage of such T cells lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the modified T cells which achieves a half-maximal inhibition of symptoms) as determined in cell culture. Sonderstrup, Springer, Sem. Immunopathol. 25: 35-45, 2003. Nikula et al, Inhal. Toxicol. 4(12j: 123-53, 2000.

The pharmaceutical composition is formulated to contain an effective amount of the present modified T cells, wherein the amount depends on the animal to be treated and the condition to be treated. The specific dose level for any particular subject depends upon a variety of factors including the activity of the specific modified T cells, the age, body weight, general health, sex, diet, time of administration, route of administration, and rate of excretion, drug combination and the severity of the particular disease undergoing therapy. An exemplary, non-limiting range for a therapeutically or prophylactically effective amount of the modified T cells of the present application is at least about $1\times10^3$ cells per dose to about $1\times10^9$ cells per dose. Other dosages are also possible, including, but not limited to, $1\times10^4$, $1\times10^5$, $1\times10^6$, $1\times10^7$, $1\times10^8$ or $1\times10^9$ cells per dose.

The modified T cells or the pharmaceutical composition can be administered alone or in combination with another therapeutic agent, e.g., chemotherapy, radiotherapy or targeted therapy or cancer vaccine.

Methods of Identifying and Culturing the Modified T Cells

In one embodiment, the methods of identifying the initial T cells and culturing the modified T cells are illustrated as in FIG. 11. Briefly, the method comprises at least the steps of: (a) obtaining a body fluid comprising mononuclear cells; (b) contacting the mononuclear cells with an inducing culturing medium comprising IL-2 and zoledronic acid to obtain a first cultured cell population; (c) contacting the first cultured cell population with a first culturing medium comprising IL-2 to obtain a second cultured cell population; and (d) contacting the second cultured cell population with a second culturing medium comprising IL-2 and IL-12 to obtain a third cultured cell population.

The culturing time of the second culturing medium comprising IL-2 and IL-12 may be critical for function of the modified T cells. In an embodiment, cells may be cultured with IL-2 and IL-12, e.g. human IL-2 and human IL-12, for 1 to 12 days, preferably 1, 2, 3, 4, 5, 6, 7, 8, 9, 10, 11, or 12 days, to generate the modified T cells. In an embodiment, cells cultured with IL-2 and IL-12 for 3, 6, 9 or 12 days generate modified T cells with similar cell yields and phenotypic patterns. In another embodiment, exposure of IL-12, e.g. 6 days, augmented cytotoxicity and antigen-presenting cell activities of the cultured cells as compared to the cells not exposed with IL-12.

In one embodiment, the composition for culturing the cells further includes IL-18. In one embodiment, the effective concentration of IL-18 is about 1 to 300 ng/mL, such as, for example, 50, 100, 150, 200, 250, 300 ng/mL. In another embodiment, the effective concentration of IL-18 is about 1.5 to about 135 ng/mL, e.g., 1.5, 3, 6, 15, 45 or 135 ng/mL, or any value or range of values there between in 10 ng/mL increments (e.g., about 30 ng/mL, about 220 ng/mL, etc.).

In another embodiment, the third culturing medium comprising IL-18 shed effect on the phenotypic patterns and the functional activities of the modified T cells. Long term IL-18 exposure may have the opposite effects on cell size, phenotype and functional activities. In an embodiment, mononuclear cells may be cultured with IL-18, e.g. human IL-18, for 1 to 12 days, preferably 1, 2, 3, 4, 5, 6, 7, 8, 9, 10, 11, or 12 days, to generate the modified T cells. In an embodiment, mononuclear cells cultured with IL-18 for 3, 6, 9 or 12 days generate modified T cells with various phenotypes. In another embodiment, adequate exposure of IL-18, e.g. 3 days, may have effects on cell size, phenotype and function of the modified T cells as compared to the cells with no IL-18 exposure.

In one embodiment, a highly purified fraction of $CD3^+$ mononuclear cells may be used in the method of the present disclosure, e.g. in contact with a culture composition comprising IL-2 and/or IL-12. In another embodiment, the $CD3^+$ mononuclear cells may be isolated after step (a) and mixed with a composition substantially consisting of hematopoietic cell medium (e.g. AIM-V), IL-2, IL-12 and serum protein (e.g. human platelet lysate). In still another embodiment, the $CD3^+$ mononuclear cells may be isolated after step (a) and mixed with a composition substantially consisting of AIM-V, IL-2, IL-12 and human platelet lysate. In one embodiment, an AIM-V medium comprises L-glutamine, streptomycin sulfate, and gentamicin sulfate.

In one embodiment, the cells are in contact with a culture composition comprising IL-2, IL-12 and/or IL-18. In another embodiment, the third cultured cell population may be mixed with a composition substantially consisting of hematopoietic cell medium (e.g. AIM-V), IL-2, IL-12, IL-18 and serum protein (e.g. human platelet lysate). In still another embodiment, the third cultured cell population may be mixed with a composition substantially consisting of AIM-V, IL-2, IL-12, IL-18 and human platelet lysate.

In another embodiment, the composition further comprises a hematopoietic cell medium. Non limiting example of the hematopoietic cell medium includes X-vivo 10, X-vivo 15, X-vivo 20 (commercially available from Lonza, Switzerland) and AIM-V (commercially available from ThermoFisher Scientific, United States).

In yet another embodiment, the composition further comprises serum protein, e.g. human platelet lysate. In the present application, "serum protein" are the proteins present in blood or plasma that serve many different functions, including transport and regulation of a cellular activity. Non limiting example of the serum protein includes enzymes, complement components, protease inhibitors, kinin precursors, serum albumin, globulins, and fibrinogen etc.

Non limiting example of the composition for culturing the cells includes (a) hematopoietic cell medium+IL-2+IL-18; (b) hematopoietic cell medium+IL-2+IL-12; (c) hematopoietic cell medium+IL-2+IL-12+IL-18; (d) X-vivo 20+IL-2+IL-18; (e) X-vivo 20+IL-2+IL-12; (f) X-vivo 20+IL-2+IL-12+IL-18; (g) AIM-V+IL-2+IL-18; (h) AIM-V+IL-2+IL-12; (i) AIM-V+IL-2+IL-12+IL-18; (j) hematopoietic cell medium+IL-2+IL-18+serum protein; (k) hematopoietic cell medium+IL-2+IL-12+serum protein; (l) hematopoietic cell medium+IL-2+IL-12+IL-18+serum protein; (m) X-vivo 20+IL-2+IL-18+serum protein; (n) X-vivo 20+IL-2+IL-12+serum protein; (o) X-vivo 20+IL-2+IL-12+IL-18+serum protein; (p) AIM-V+IL-2+IL-18+serum protein; (q) AIM-V+IL-2+IL-12+serum protein; and (r) AIM-V+IL-2+IL-12+IL-18+serum protein.

In one embodiment, the composition is used for culture the modified T cells, in the presence of 5% $CO_2$ at 37° C.

The culturing medium according to some embodiments of the application enhances the proliferation of the modified T cells. In one embodiment, the culturing medium substantially enhance the expression of CXCR4 cell surface antigens. In one embodiment, the culturing medium substantially enhance the expression of CD11c and CXCR4 cell surface antigens and reduce the expression of CXCR3 cell surface antigens on the modified T cells. In another embodiment, the culturing medium enhances the expression of CD69, CD11c, CXCR4 cell surface antigens and residues the expression of CXCR3 cell surface antigen on the modified T cells. Proliferation rate of the modified T cells was determined by the purity of $CD3^+$ cells via FACS and viable counts. Other assays for cell proliferation are well known in the art, e.g., clonogenic assays, metabolic assays, and direct proliferation assays.

An exemplary non-limiting range for the contact time of the $CD3^+$ mononuclear cells and the inducing culturing medium is from about 1 minute to about 1 hour, from about 1 hour to about 24 hours, from about 1 day to about 3 days, from about 1 day to about 6 days, from about 1 day to about 9 days, from about 1 day to about 12 days, from about 3 days to about 6 days, from about 3 days to about 9 days, from about 3 days to about 12 days, from about 6 days to about 9 days, from about 6 days to about 12 days, or at least 1 day. In one embodiment, the contact time is about 3 days. In another embodiment, the contact time is about 6 days.

An exemplary non-limiting range for the contact time of the first cultured cell population and the first culturing medium is from about 1 minute to about 1 hour, from about 1 hour to about 24 hours, from about 1 day to about 3 days, from about 1 day to about 6 days, from about 1 day to about 9 days, from about 1 day to about 12 days, from about 3 days to about 6 days, from about 3 days to about 9 days, from about 3 days to about 12 days, from about 6 days to about 9 days, from about 6 days to about 12 days, or at least 1 day. In one embodiment, the contact time is about 3 days. In another embodiment, the contact time is about 6 days.

An exemplary non-limiting range for the contact time of the second cultured cell population and the second culturing medium is from about 1 minute to about 1 hour, from about 1 hour to about 24 hours, from about 1 day to about 3 days, from about 1 day to about 6 days, from about 1 day to about 9 days, from about 1 day to about 12 days, from about 3 days to about 6 days, from about 3 days to about 9 days, from about 3 days to about 12 days, from about 6 days to about 9 days, from about 6 days to about 12 days, or at least 1 day. In one embodiment, the contact time is about 3 days. In another embodiment, the contact time is about 6 days.

An exemplary non-limiting range for the contact time of the third cultured cell population and the third culturing medium is from about 1 minute to about 1 hour, from about 1 hour to about 24 hours, from about 1 day to about 3 days, from about 1 day to about 6 days, from about 1 day to about 9 days, from about 1 day to about 12 days, from about 3 days to about 6 days, from about 3 days to about 9 days, from about 3 days to about 12 days, from about 6 days to about 9 days, from about 6 days to about 12 days, or at least 1 day. In one embodiment, the contact time is about 3 days. In another embodiment, the contact time is about 6 days.

In one embodiment, the mononuclear cells are in contact with a inducing culturing medium comprising an IL-2 and zoledronic acid; followed by contacting with a first culturing medium comprising IL-2. In one embodiment, the mononuclear cells are in contact with a inducing culturing medium comprising an IL-2 and zoledronic acid; contacting with a first culturing medium comprising IL-2; and contacting with a second culturing medium comprising IL-2 and IL-12. In one embodiment, the mononuclear cells are in contact with a inducing culturing medium comprising an IL-2 and zoledronic acid; contacting with a first culturing medium comprising IL-2; contacting with a second culturing medium comprising IL-2 and IL-12; and contacting with a third culturing medium comprising IL-2, IL-12 and IL-18. In another embodiment, the inducing culturing medium, the first culturing medium and the second culturing medium further comprise a hematopoietic cell medium, such as AIM-V or X-vivo, and/or a serum protein, such as human platelet lysate.

The following examples of specific aspects for carrying out the present invention are offered for illustrative purposes only, and are not intended to limit the scope of the present invention in any way.

EXAMPLES

Example 1: Addition of IL-12 Plays Major Role in Phenotype and Functional Development of the Modified T Cells Mononuclear cells were cultured in three groups (FIG. 1). In Group N, the mononuclear cells were cultured in AIM-V medium in the presence of 60 ng/mL human recombinant IL-2 (hIL-2), 2% (v/v) human platelet lysate (HPL) and 5 µM zoledronic acid for 3 days. Subsequently, the cells were subcultured in AIM-V medium in the presence of 120 ng/mL hIL-2 and 4% (v/v) HPL every three days and harvested on day 15. In Group A, the mononuclear cells were cultured in AIM-V medium in the presence of 60 ng/mL hIL-2, 2% (v/v) HPL and 5 µM zoledronic acid for 3 days. Subsequently, the cells were subcultured in AIM-V medium in the presence of 120 ng/mL hIL-2 and 4% (v/v) HPL on day 3 and 6, subcultured in AIM-V medium in the presence of 120 ng/mL hIL-2, 4% (v/v) HPL and 8 ng/mL human recombinant IL-12 (hIL-12) on day 9 and 12, and harvested on day 15. In Group B, the mononuclear cells were cultured in AIM-V medium in the presence of 60 ng/mL hIL-2, 2% (v/v) HPL and 5 µM zoledronic acid for 3 days. Subsequently, the cells were subcultured in AIM-V medium in the presence of 120 ng/mL hIL-2 and 4% (v/v) HPL on day 3 and 6, subcultured in AIM-V medium in the presence of 120 ng/mL hIL-2, 4% (v/v) HPL and 45 ng/mL human recombinant IL-18 (hIL-18) on day 9 and 12, and harvested on day 15.

Cell numbers in each group were counted by using trypan blue dye exclusion. Furthermore, the cells were subsequently stained with monoclonal antibodies (mAbs) of CD69, CD11c, CXCR4 and CXCR3. Samples were acquired and analyzed via Navios Flow Cytometer while the data analysis was done via Kaluza software (Beckman Coulter).

Figure 2:
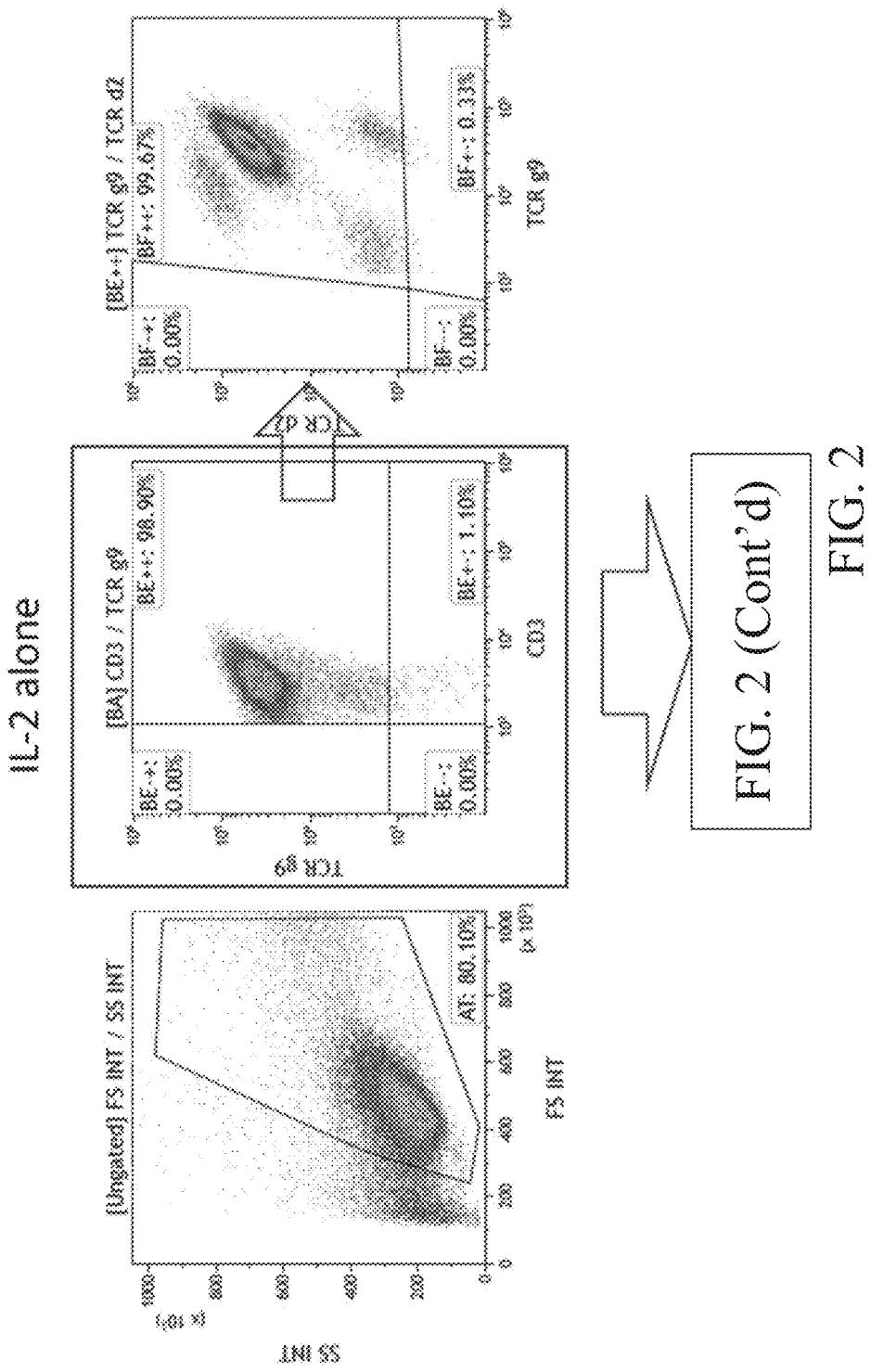
FIG. 2 illustrates an assembly of flow cytometry images of the T cells cultured in the culturing medium with IL-2 alone for expression of CD69, CD11c, CXCR4 and CXCR3. Particularly, isolated PBMCs were cultured in vitro with Zoledronic acid and IL-2 first. Additional IL-2 was added into culture medium every 3 days until day 12 and cells were harvested on day 15. The T cells in total cell population are more than 90%. In addition, the T cells cultured with IL-2 only expressed low CD69 and CD11c, dim CXCR4 and high CXCR3.
Figure 2:
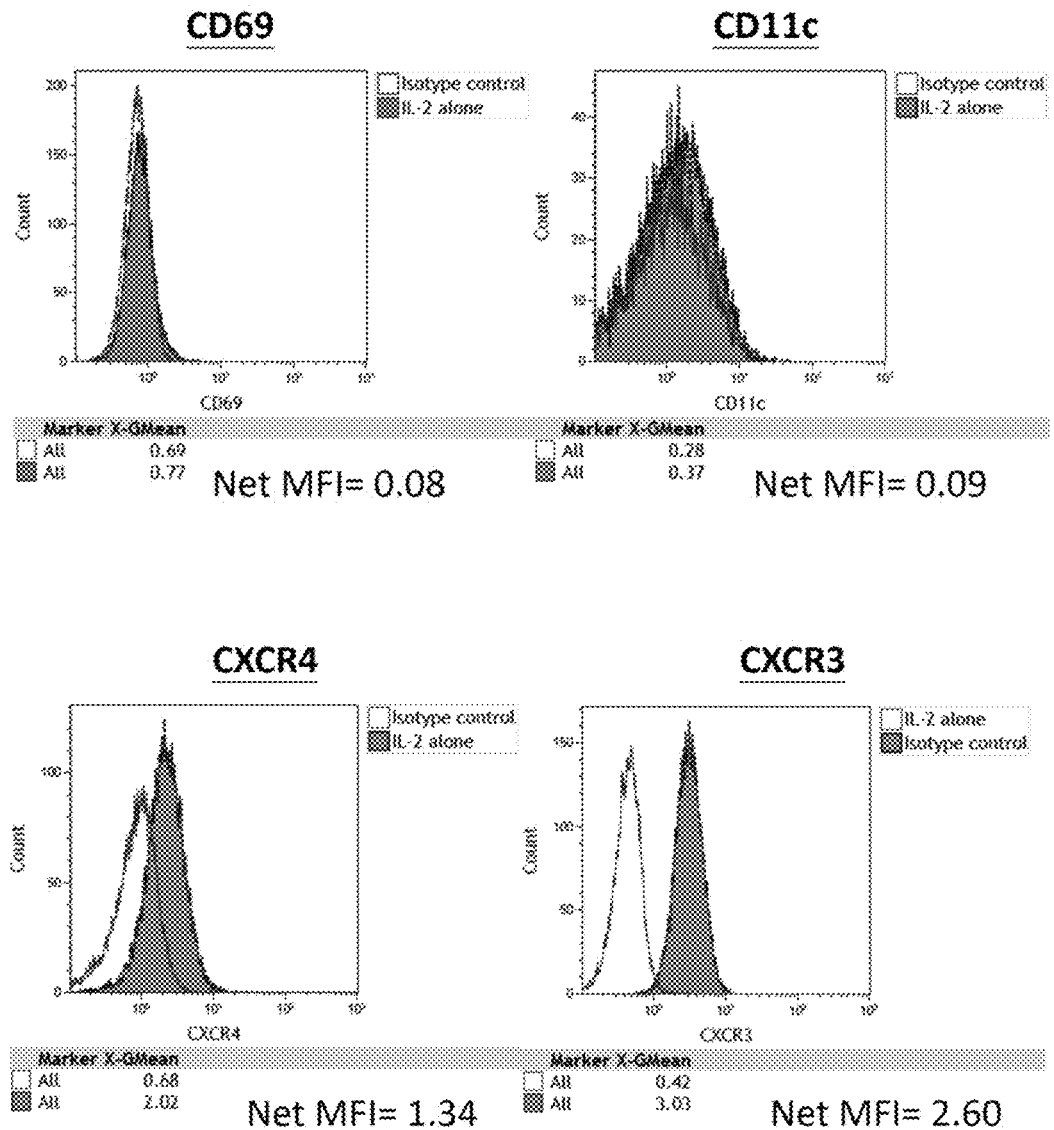
Figure 3:
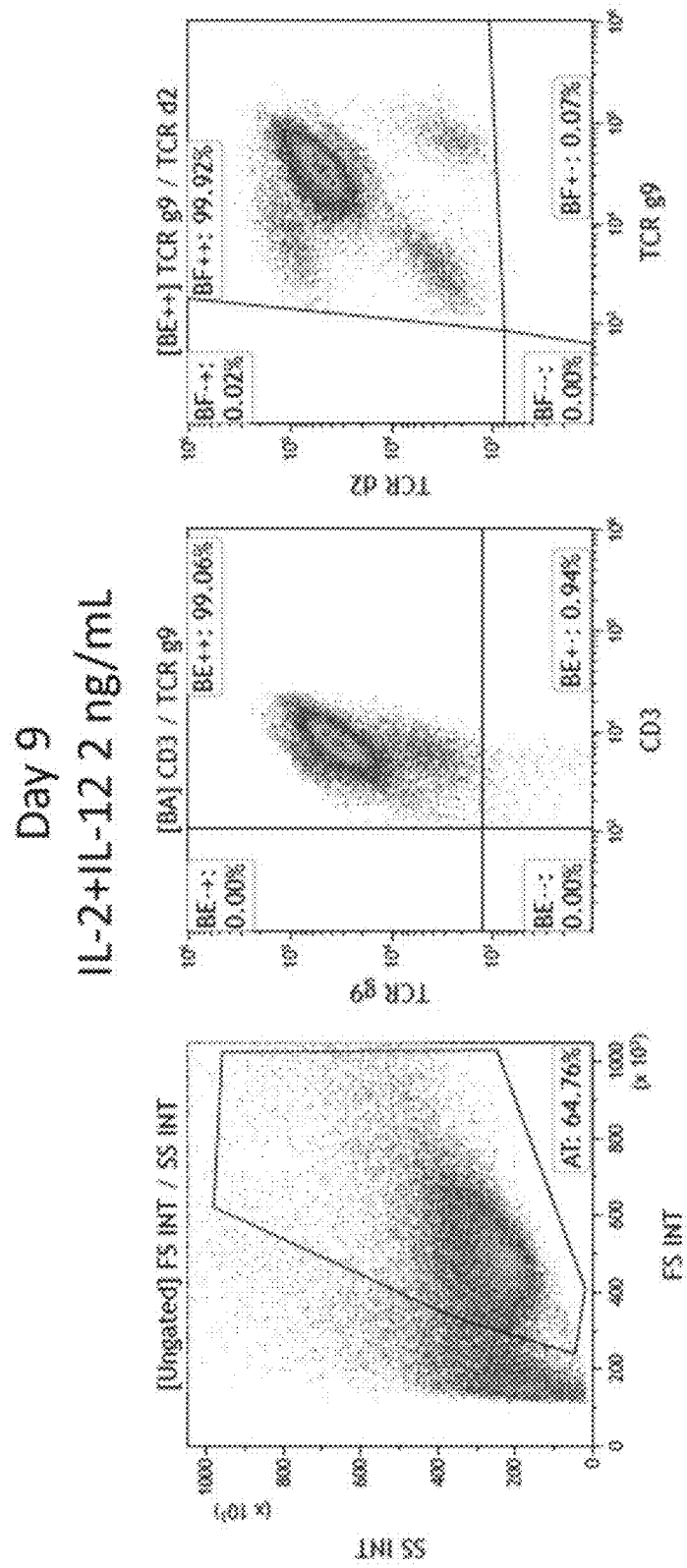
FIG. 3 illustrates an assembly of flow cytometry images of the modified T cells cultured the culturing medium having the IL-2 added with IL-12 at day 9 for expression of CD69, CD11c, CXCR4 and CXCR3. Particularly, cytokine IL-12 was added into culture medium with IL-2 on day 9 to day 12 and cells were harvested on day 15. The modified T cells in total cell population are also more than 90%. In addition, the modified T cells cultured in the culturing medium with IL-12 added on day 9 expressed more CD69, CD11c, CXCR4 and less CXCR3 than cultured with IL-2 only.
Figure 3:
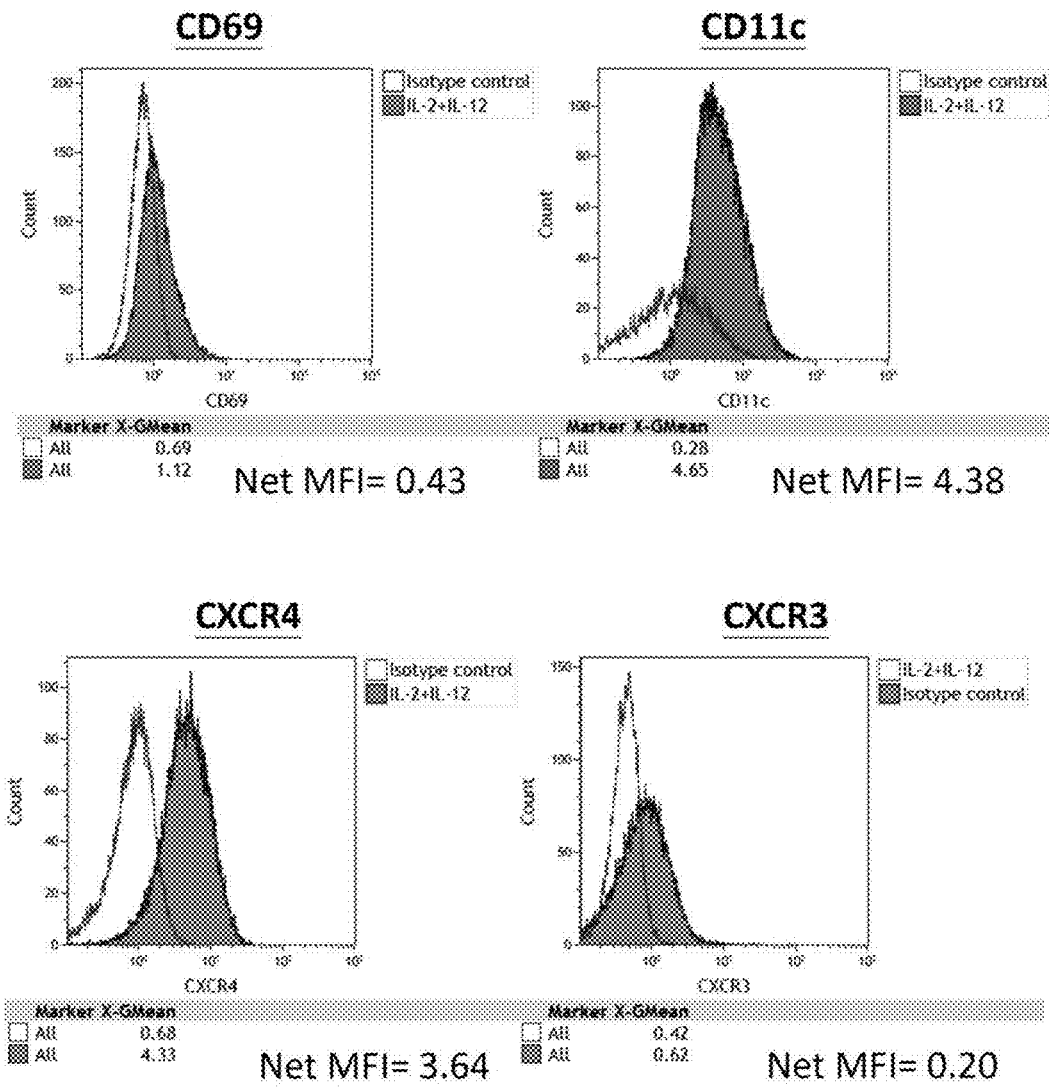
Figure 4:
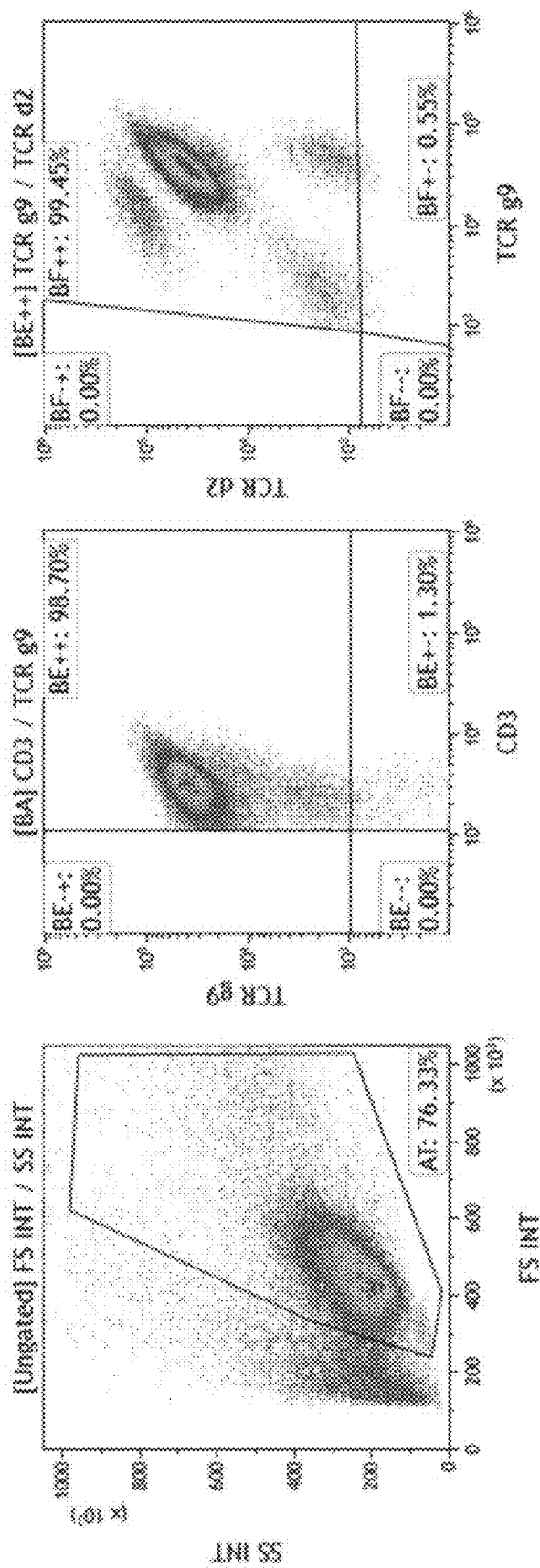
FIG. 4 illustrates an assembly of flow cytometry images of the T cells cultured IL-2 added with 45 ng/mL IL-18 for expression of CD69, CD11c, CXCR4, and CXCR3. Particularly, 45 ng/mL cytokine IL-18 was added into culture medium with IL-2 on day 9 to day 12 and cells were harvested on day 15. The T cells in total cell population are also more than 90%. The cell surface marker expression on the T cells cultured with IL-18 on day 9 showed no differences comparing with IL-2 alone.
Figure 4:
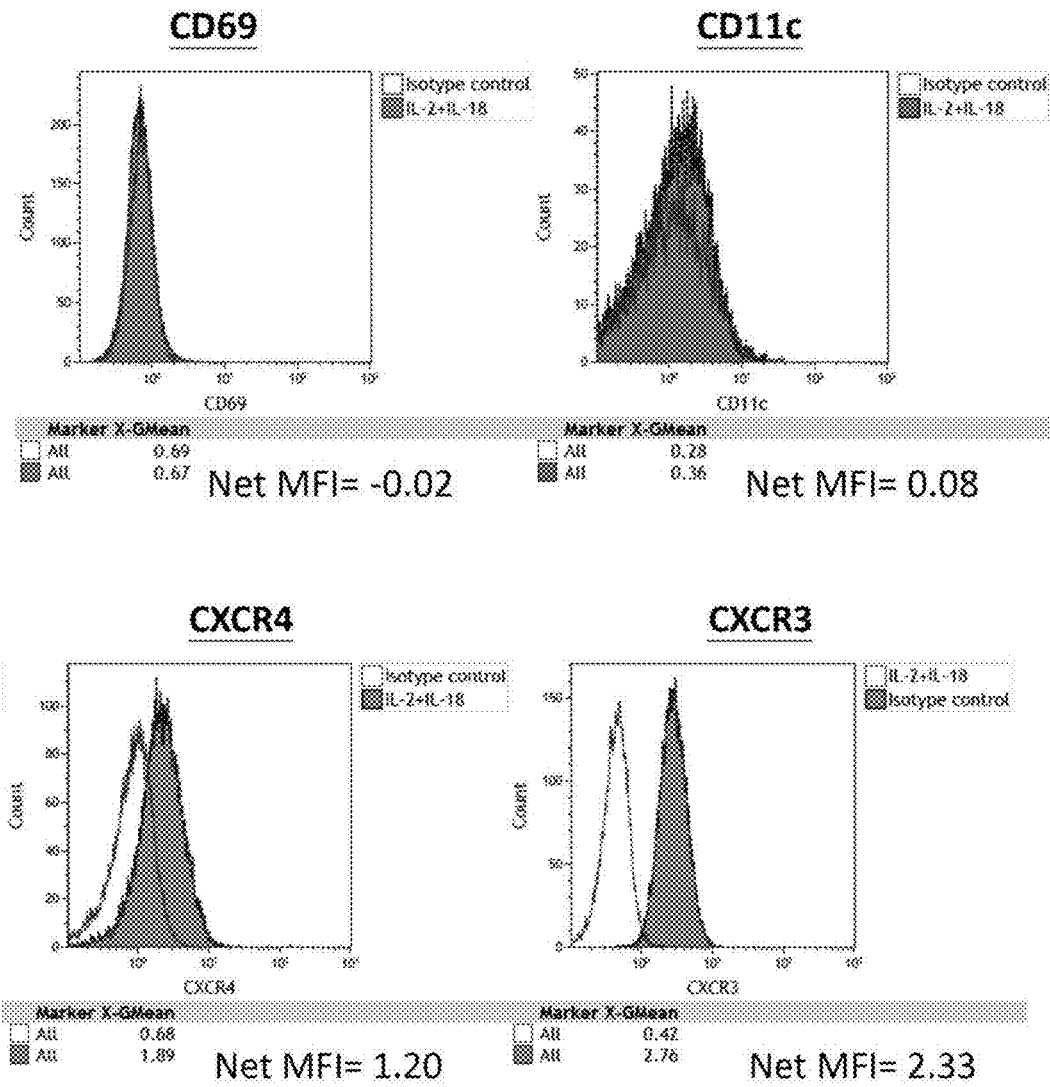

According to the cell count data, the cell number of the group A and the Group B are less the group N, indicating that the addition of IL-12 or IL-18 to culture medium causes cell yield lose (data not shown). In addition, using IL-2+IL-12 or IL-2+IL-18 conducted γδ T cell did not affect on cell purity comparing to IL-2 alone (FIGS. 3-4). Using IL-2+IL-12 conducted γδ T cell could express higher surface markers, such as CD11c and CXCR4, intensity and CXCR3 down regulation comparing to IL-2 alone (FIGS. 2-3). However, using cytokine IL-2+IL-18 did not have significant difference comparing to IL-2 alone (FIGS. 2 and 4). In other words, using IL-2+IL-12 group have better performance in surface marker expression on CD69, CD11c and CXCR4 and down regulation on CXCR3 than IL-2 alone (FIGS. 2 and 4).

On the other hand, functional assays were also performed to evaluate cytotoxicity and antigen-presentation activity. Evaluation of cytotoxicity of the modified T cells was performed by PanToxilux kit (OncoImmunin, Inc.). Human chronic myelogenous leukemia (CML) cell line, K562, served as a target cell and stained with TFL4 under the optimal concentration for 50 minutes. Co-incubation of TFL4 labeled target cell and the cultured cells with the caspase substrate under 37° C. for 20 minutes. The cells were harvested and analyzed the signal of TFL-4$^+$substrate$^+$ via flow cytometry. Evaluation of the activity of antigen-presentation of the cultured cells was performed by mixed lymphocyte reaction (MLR). Responder cells (CD25-PBMCs) were enriched and stained with CellTracei Violet-cell proliferation kit (Invitrogen). Co-culture of CellTrace Violet-labeled CD25-PBMCs and the modified T cells under 37° C. for 5 days. The cells were harvested and analyzed the CellTrace Violet-diluted pattern via flow cytometry. According to the results shown in FIG. 5, using IL-2+IL-12 would promote killing activity of the modified T cells comparing to IL-2 alone and IL-2+IL-18. In addition, IL-2+IL-12 would also promote the expression of IFN-γ (FIG. 9) and the antigen presenting activity (FIG. 10) of the modified T cells comparing to IL-2 alone.

To sum up, the addition of IL-12 on day 9 may achieve the balance between cell yield and killing activity. However, the group B make no difference in cell mark expression and even lose killing activity comparing to IL-2 alone. Thus, the group A, i.e. IL-2+IL-12, was chosen in promoting γδ T into new cell type.

Figure 6:
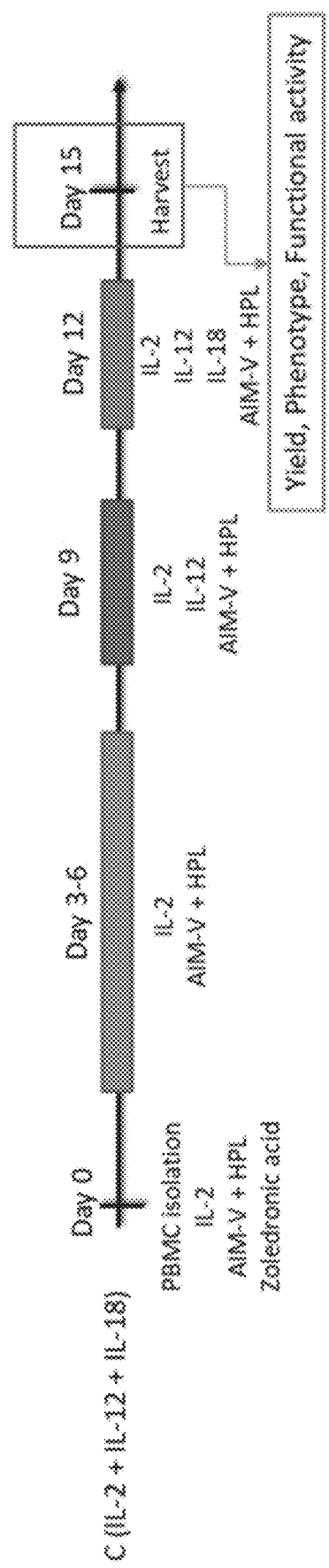
FIG. 6 illustrates the experimental design to determine the adequate cytokine concentration for the phenotype and functional development of the modified T cells.

Example 2: Addition of IL-18 in Late Stage Plays Major Role in Phenotype and Functional Development of the Modified T Cells Mononuclear cells were cultured in two groups. In Group A (FIG. 1), the mononuclear cells were cultured in AIM-V medium in the presence of 60 ng/mL hIL-2, 2% (v/v) HPL and 5 μM zoledronic acid for 3 days. Subsequently, the cells were subcultured in AIM-V medium in the presence of 120 ng/mL hIL-2 and 4% (v/v) HPL on day 3 and 6, subcultured in AIM-V medium in the presence of 120 ng/mL hIL-2, 4% (v/v) HPL and 2 ng/mL hIL-12 on day 9 and 12, and harvested on day 15. In the group C (FIG. 6), the treatments of the mononuclear cells on day 0, 3, 6 and 9 were the same as those in the Group A. However, the cells in Group C were subcultured in AIM-V medium in the presence of 120 ng/mL hIL-2, 4% (v/v) HPL, 2 ng/mL hIL-12 and 135, 45 or 15 ng/mL human recombinant IL-18 (hIL-18) on 12, and harvested on day 15. The cultured cells were counted by using trypan blue dye exclusion and stained with mAbs of CD69, CD11c, CXCR4 and CXCR3. Samples were acquired and analyzed via Navios Flow Cytometer while the data analysis was done via Kaluza software (Beckman Coulter).

Figure 5:
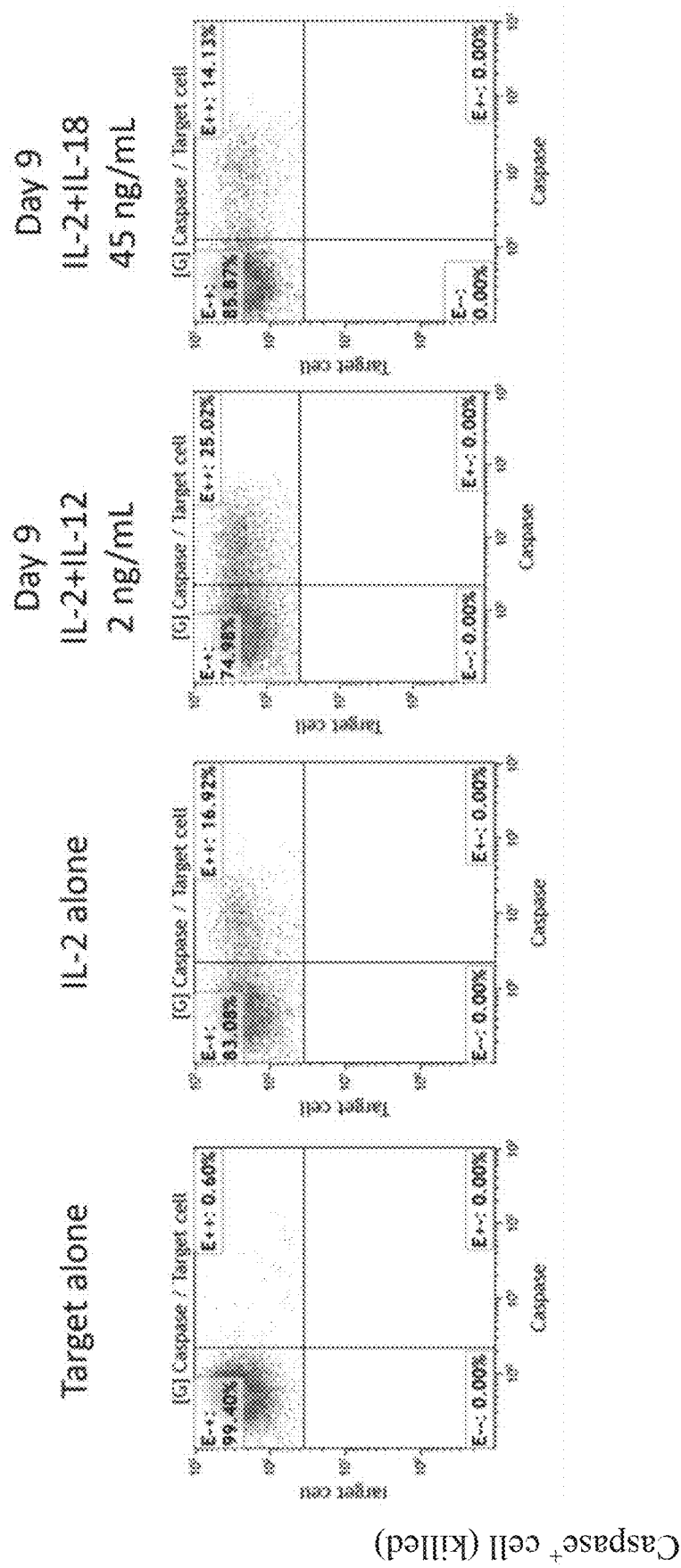
FIG. 5 illustrates the cytotoxicity mediated by the T cell cultured with the culturing medium comprising IL-2 only or IL-2+IL-18, or the modified T cell cultured with the culturing medium comprising IL-2+IL-12. Culturing medium comprising IL-2+IL-12 added on day 9 provided the best target cell (K562) killing activity (caspase positive K562: 25.02%) comparing with IL-2 alone (caspase positive K562: 16.92%) and IL-2+IL-18 added on day 9 (caspase positive K562: 14.13%).
Figure 7A:
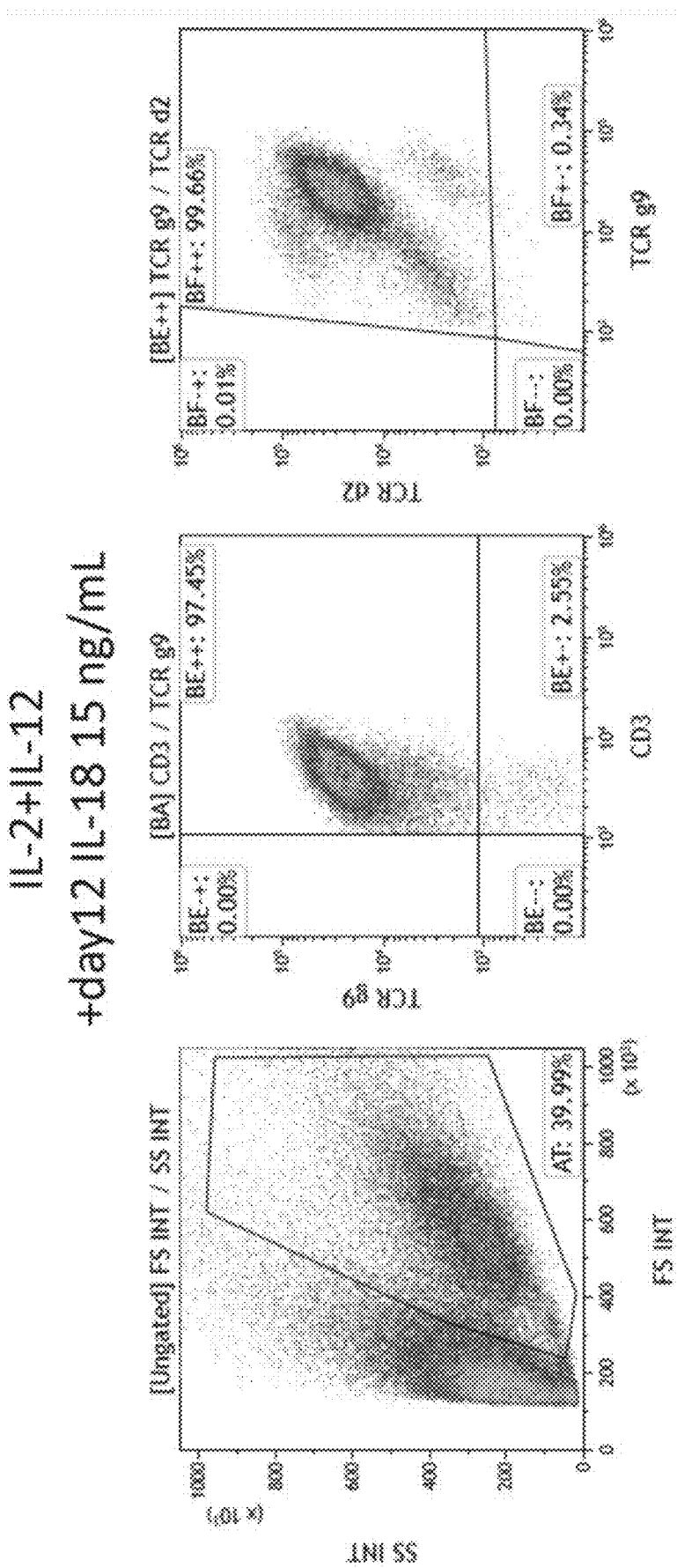
FIG. 7A illustrates an assembly of flow cytometry images of the modified T cells cultured in IL-2 added with IL-12 and IL-12+15 ng/mL IL-18 on day 9 and 12, respectively, for expression of CD69, CD11c, CXCR4, and CXCR3.
Figure 7A:
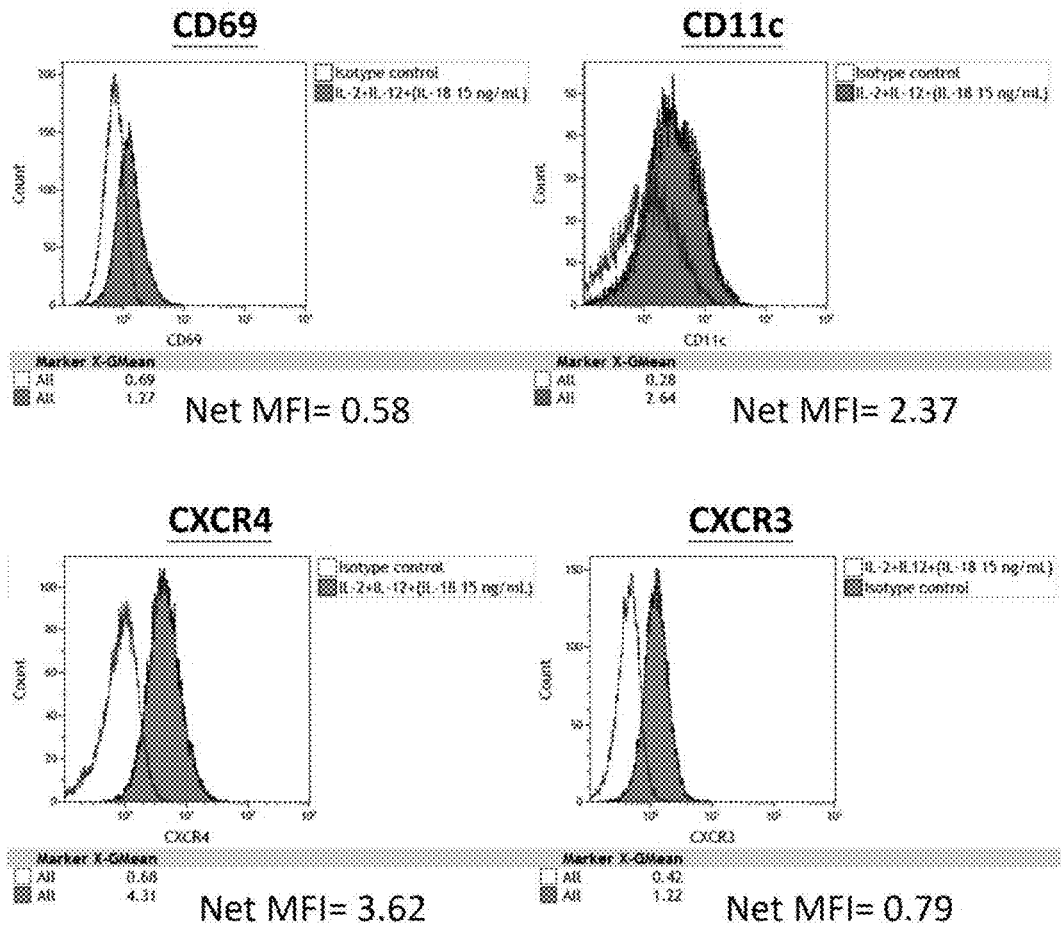
Figure 7B:
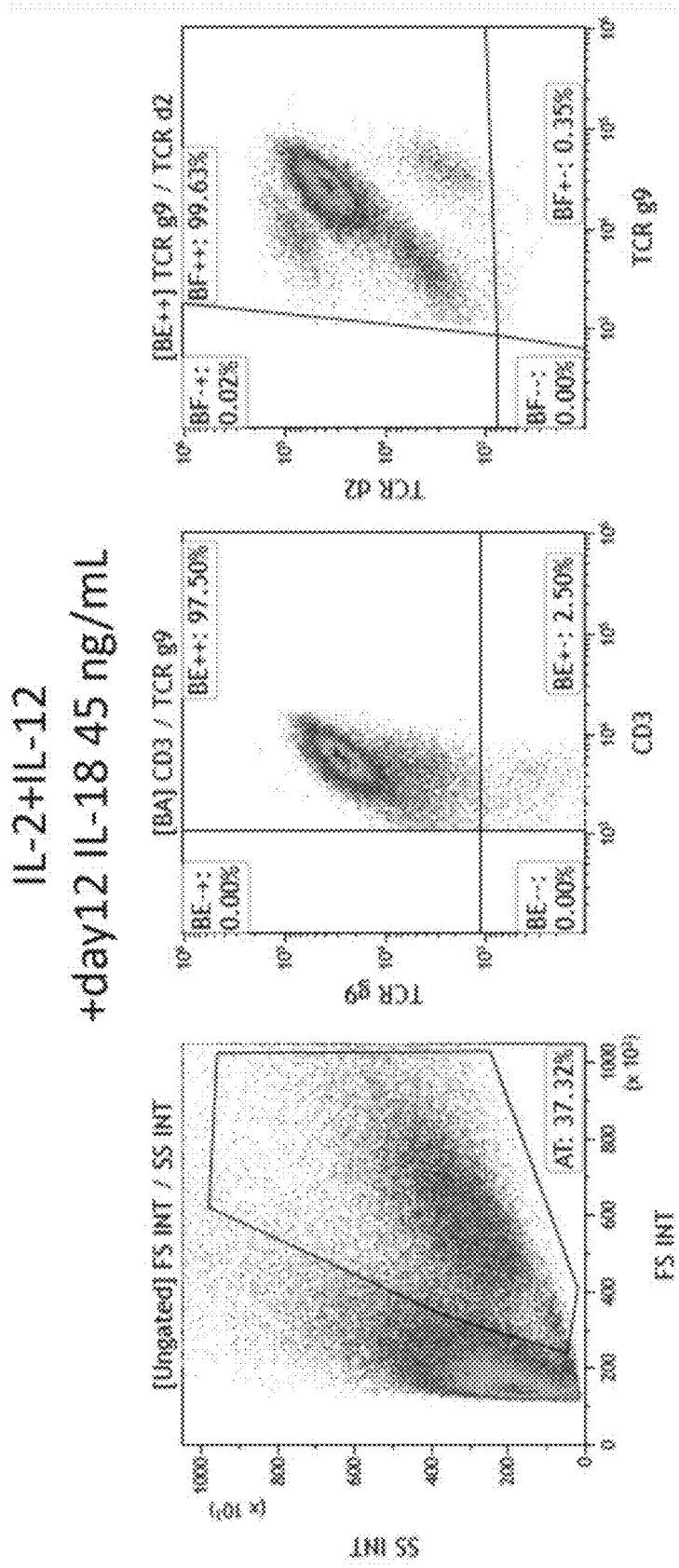
FIG. 7B illustrates an assembly of flow cytometry images of the modified T cells cultured in IL-2 added with IL-12 and IL-12+45 ng/mL IL-18 on day 9 and 12, respectively, for expression of CD69, CD11c, CXCR4, and CXCR3.
Figure 7B:
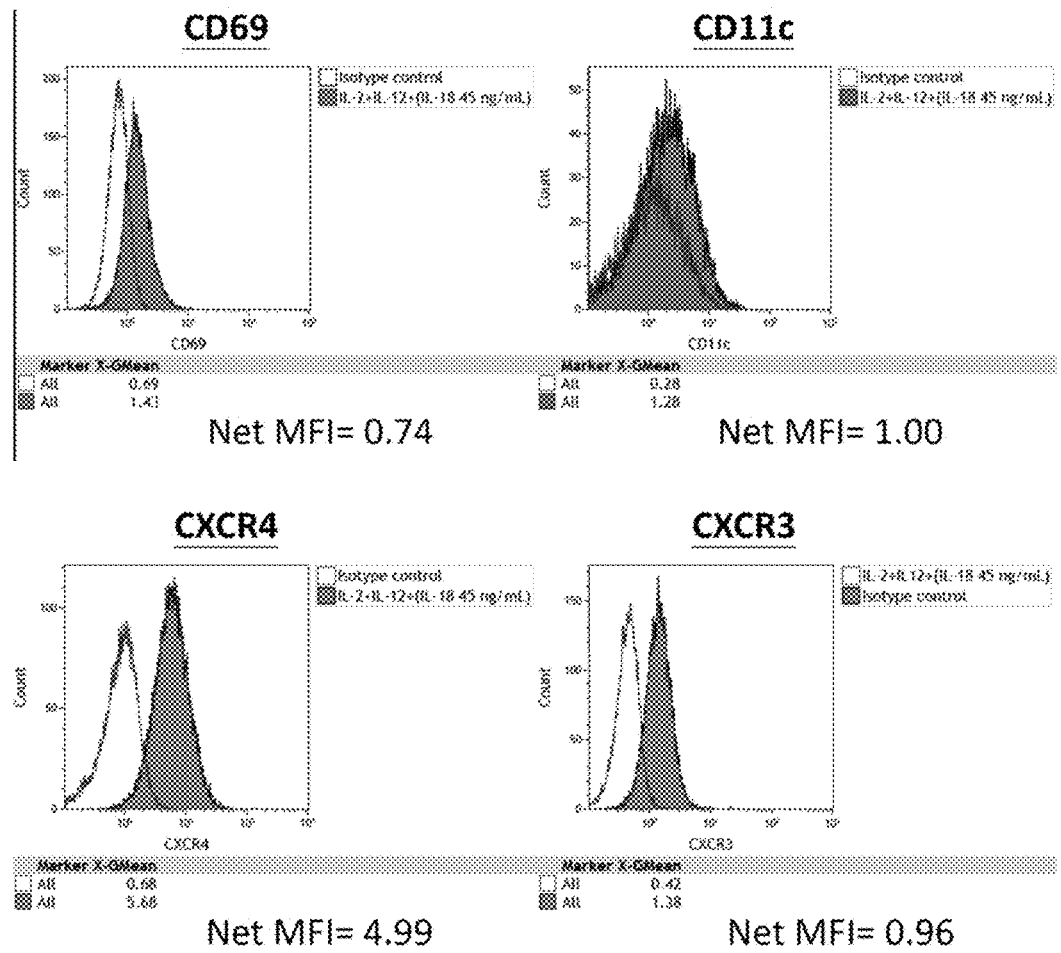
Figure 7C:
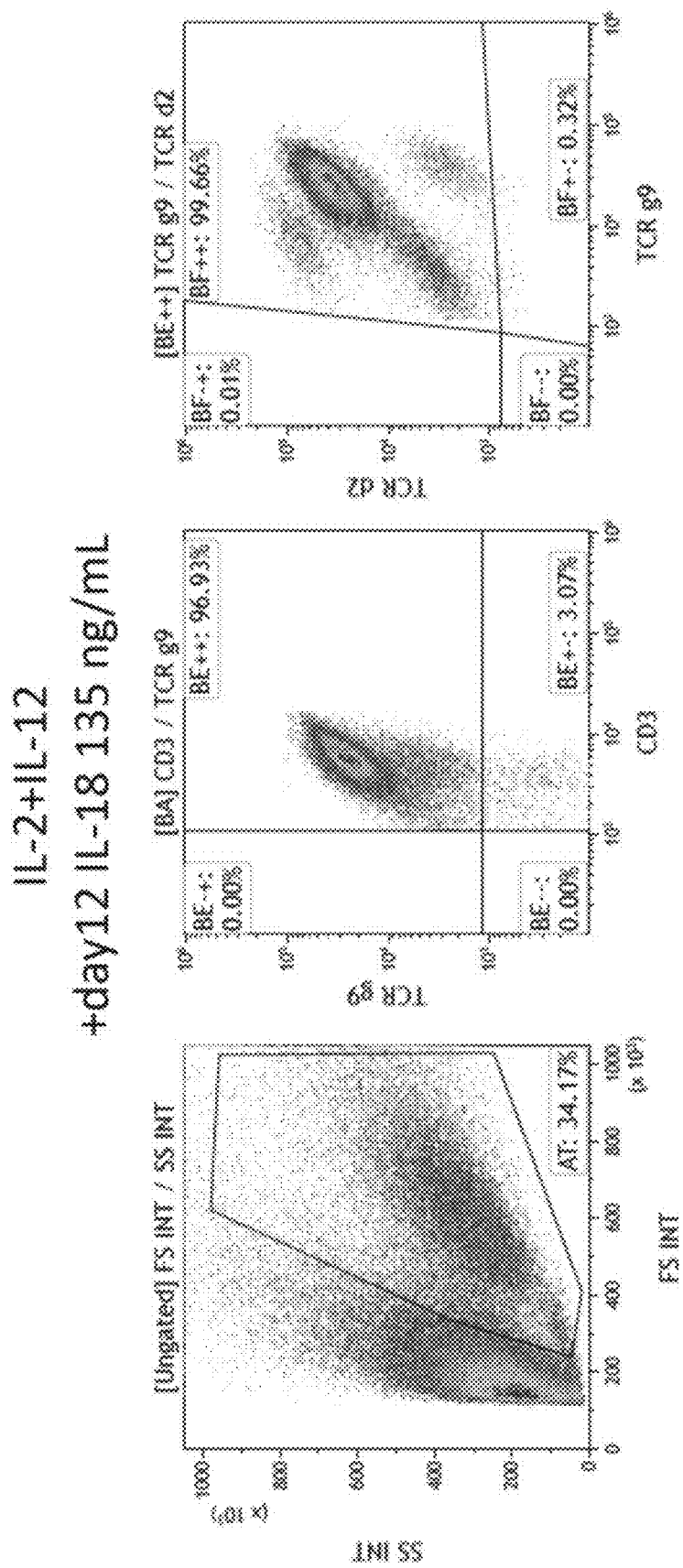
FIG. 7C illustrates an assembly of flow cytometry images of the modified T cells cultured in IL-2 added with IL-12 and IL-12+135 ng/mL IL-18 on day 9 and 12, respectively, for expression of CD69, CD11c, CXCR4, and CXCR3. Particularly, cytokine IL-12 was added into culture medium with IL-2 on day 9. Different concentration of cytokine IL-18 was added into culture medium with IL-2 and IL-12 on day 12. The modified T cells in total cell population were also more than 95%. The cell surface expression intensity of CD69, CXCR4 and CXCR3 were higher than culture condition IL-2+IL-12 added on day 9. However, the CXCR3 expression intensity was still lower than IL-2 alone.
Figure 7C:
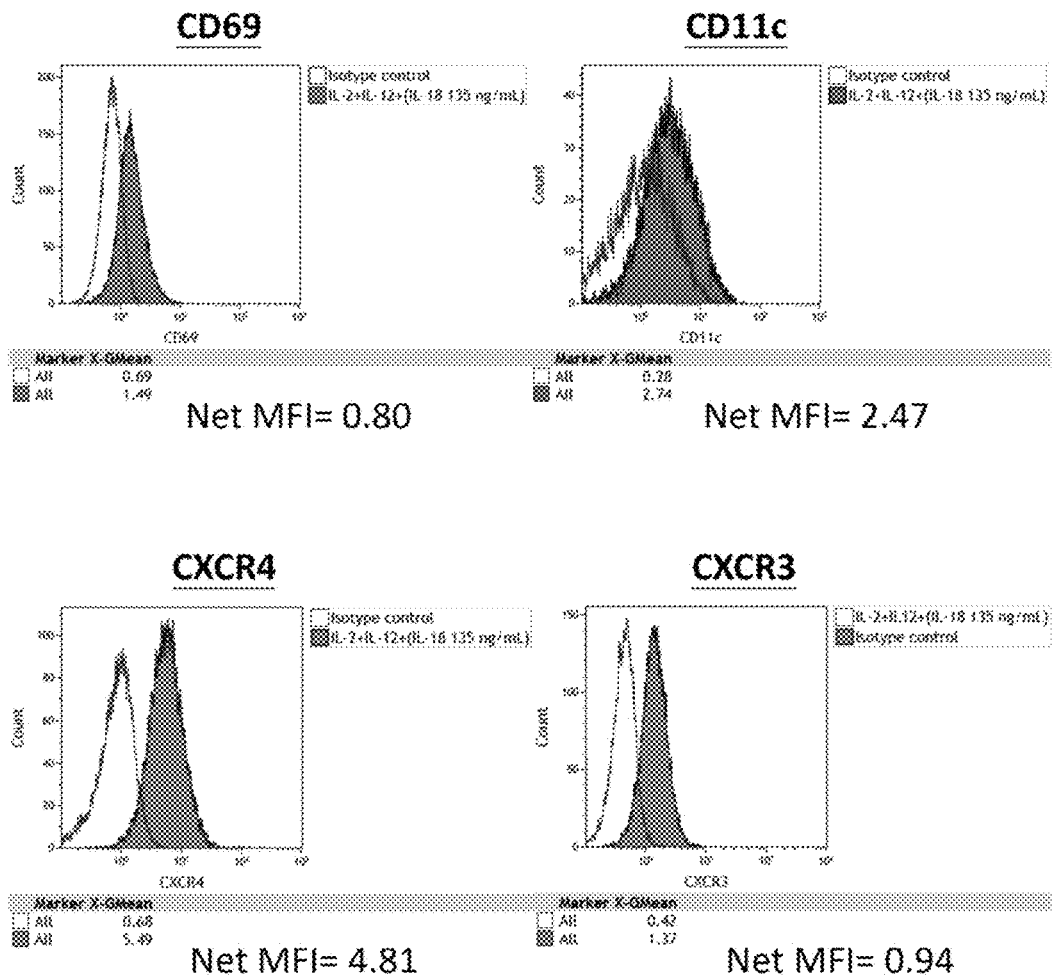
Figure 8:
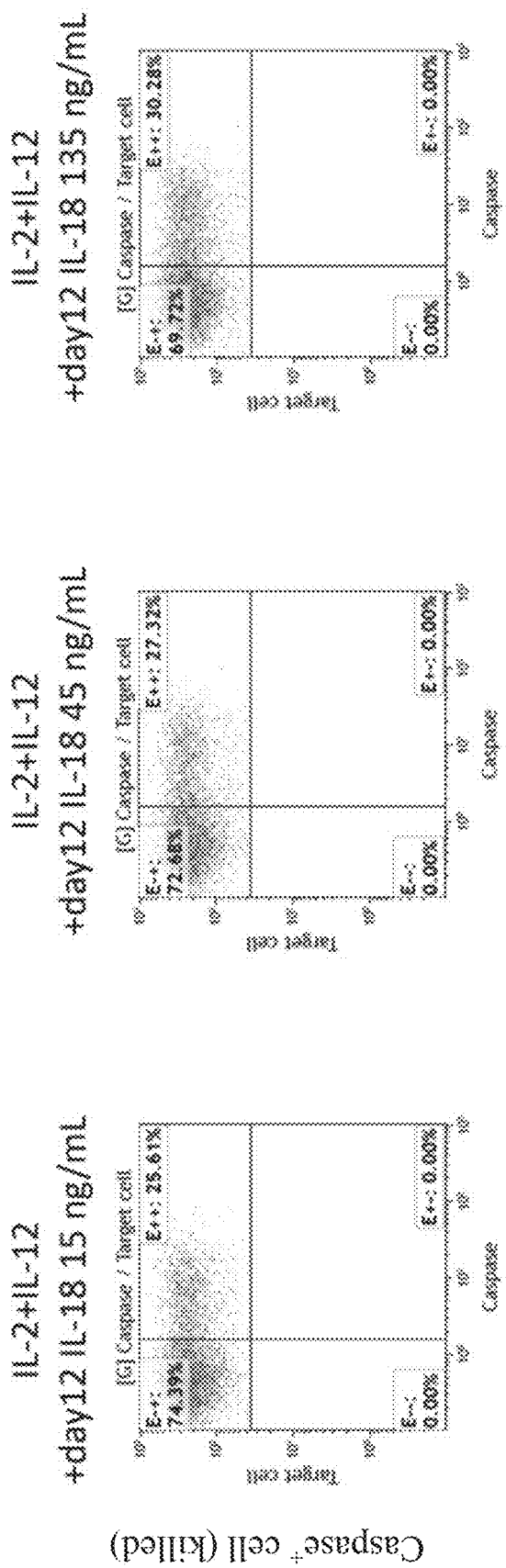
FIG. 8 illustrates the cytotoxicity mediated by the modified T cell cultured with the culturing medium comprising IL-2+IL-12+various concentration of IL-18 added on day 12. The target cell (K562) killing activity in different concentration of cytokine IL-18 added into culture medium comprising IL-2+IL-12 on day 12 were not worse than the culture condition IL-2+L-12 added on day 9.
Figure 9:
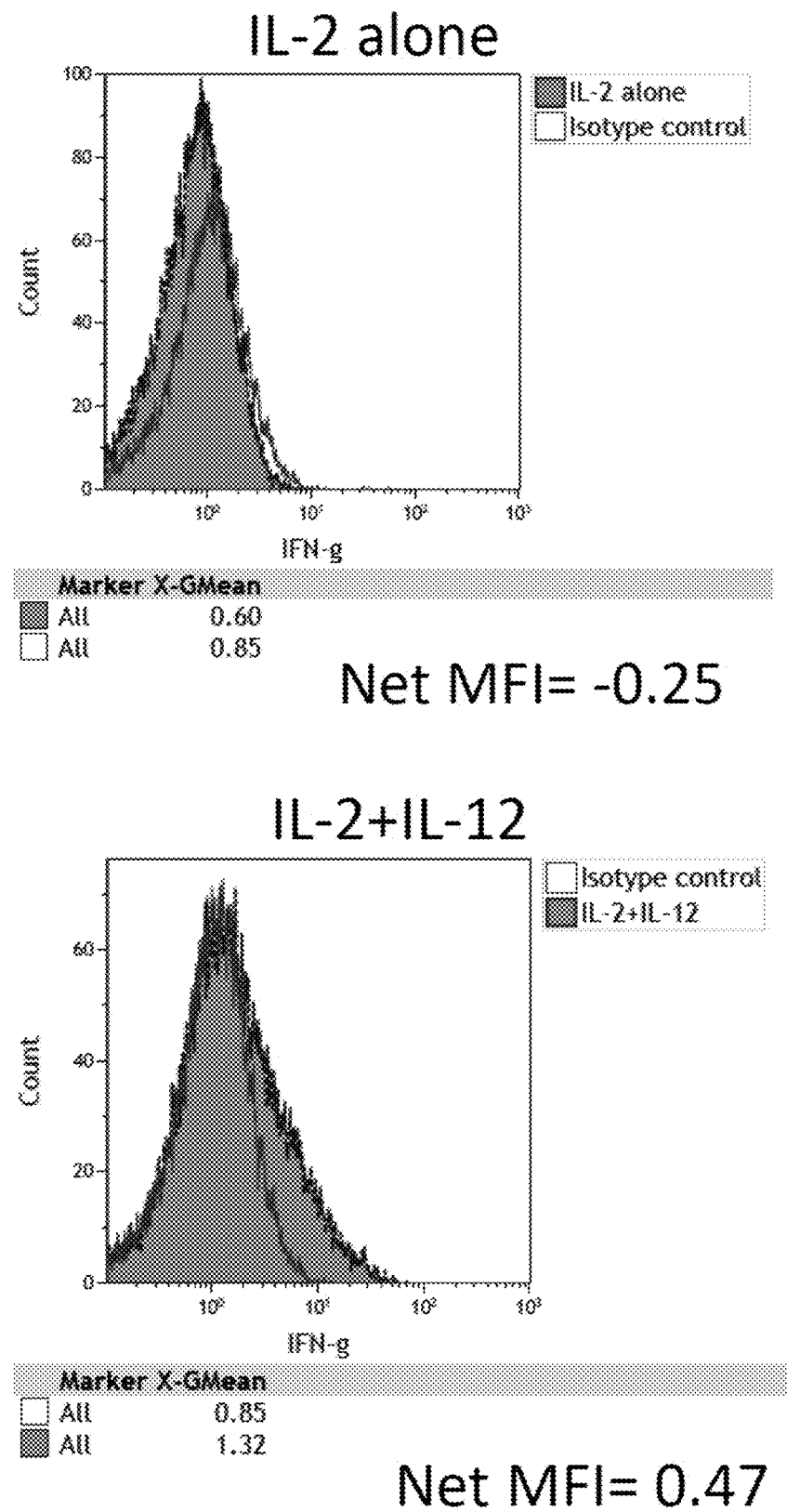
FIG. 9 illustrates an assembly of flow cytometry images of the modified T cells cultured with IL-2 alone, IL-2+IL-12 and IL-2+IL-12+various doses of IL-18 for expression of IFN-γ. The production of IFN-γ in IL-2+IL-12+various doses of IL-18 added on day 12 were significantly higher than IL-2+IL-12 and IL-2 alone.
Figure 9:
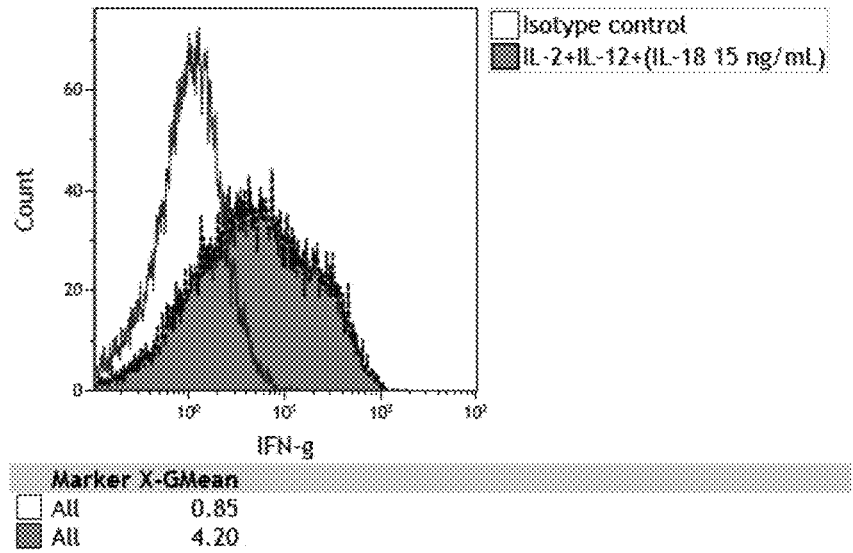
Figure 9:
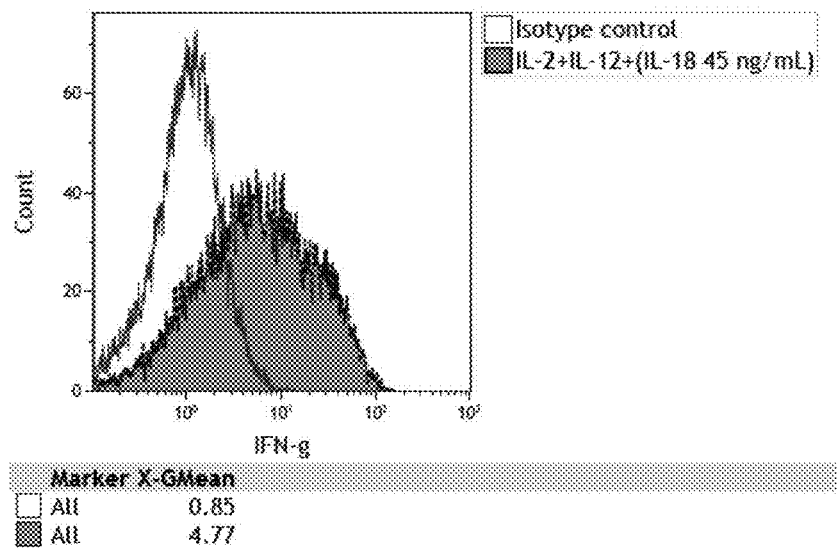
Figure 9:
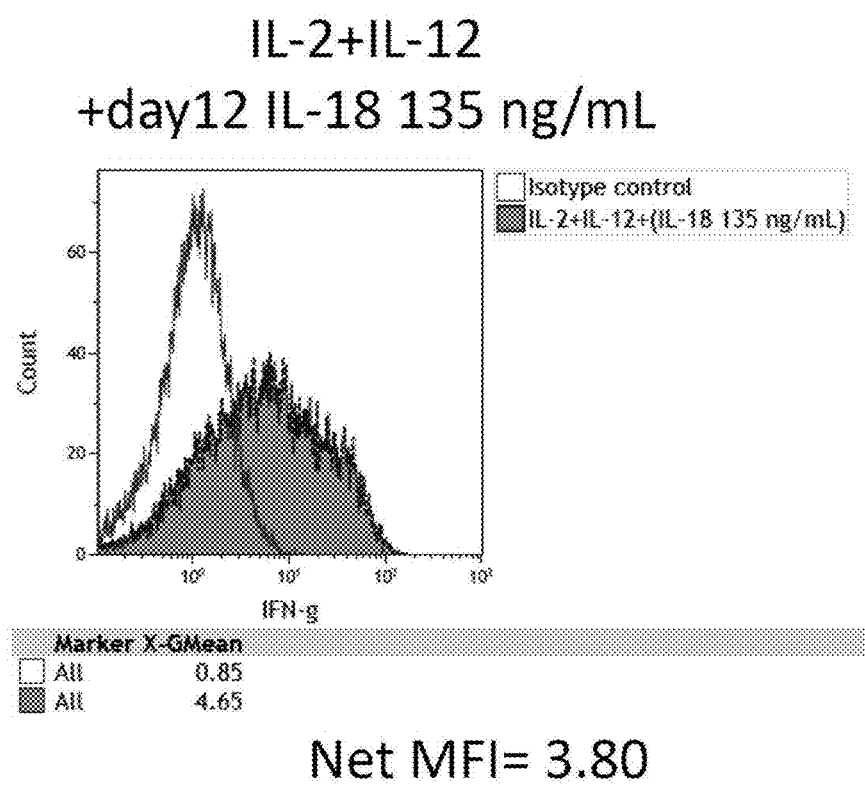
Figure 10:
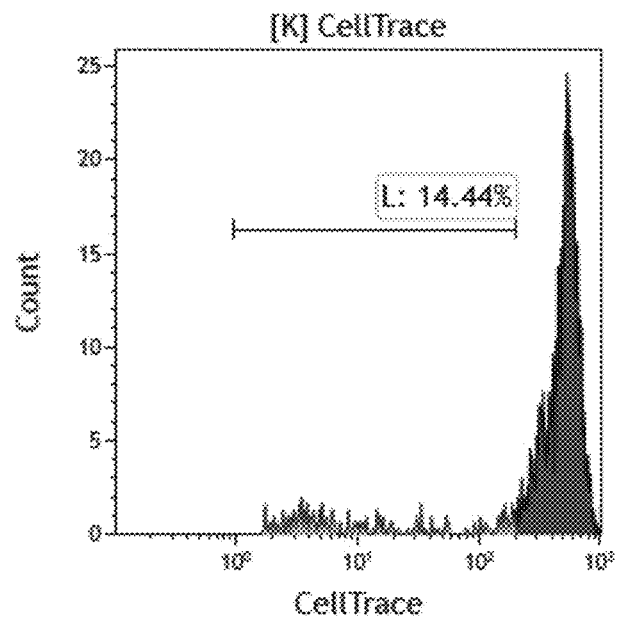
FIG. 10 illustrates the antigen presenting activity mediated by the modified T cells cultured with IL-2 alone, IL-2+IL-12 and IL-2+IL-12+various doses of IL-18. Particularly, the proliferation of CD8 T cells test by allogeneic mix lymphocyte reaction indicated that all of the modified T cells cultured in the culturing medium comprising IL-2+IL-12 and IL-2+IL-12+various doses of IL-18 are more effective than IL-2 alone on antigen presenting activity. However, the antigen presenting activity shows no difference between IL-2+IL-12+various doses of IL-18 and IL-2+IL-12.
Figure 10:
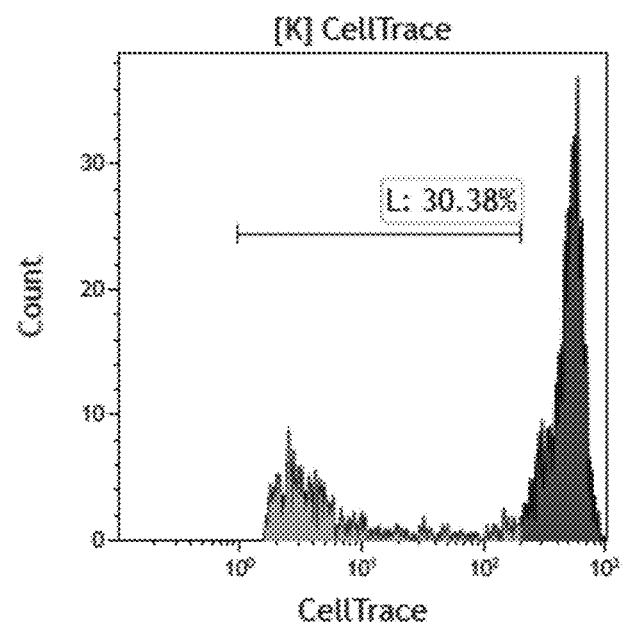
Figure 10:
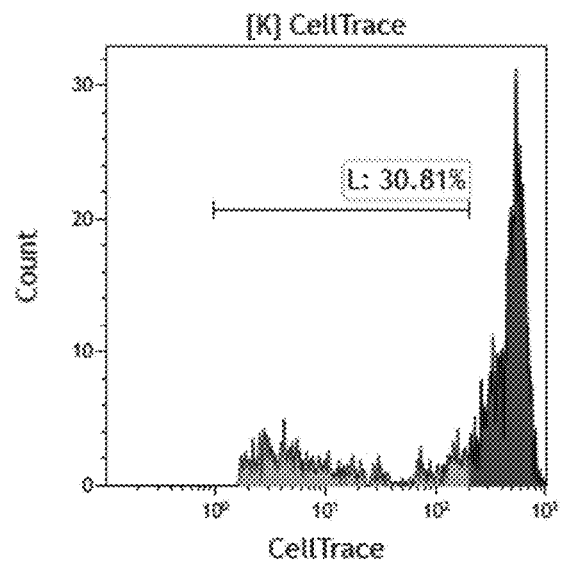
Figure 10:
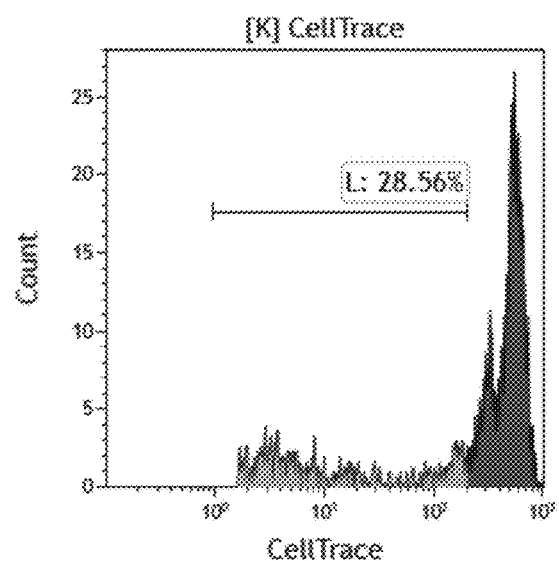
Figure 10:
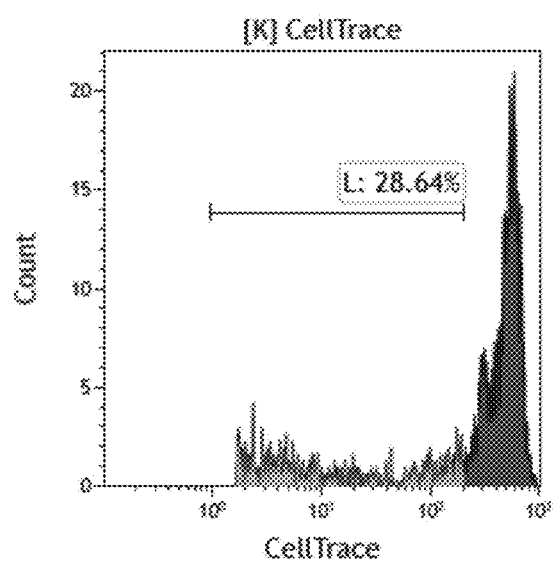

According the cell count data (Table 3), the fold change in the cell number of the group C are less the group A, indicating that the further addition of IL-18 to the culture medium on day 12 causes cell yield lose. However, medium comprising IL-2+IL-12+IL-18 has no significant effects on cell purity comparing to medium comprising IL-2+IL-12 (data not shown). Using IL-2+IL-12+IL-18 conducted γδ T cell on day 12 could generally express higher net mean fluorescence intensity (MFI) in surface markers, such as CD69, CXCR4 and CXCR3, comparing to IL-2+IL-12 (FIGS. 7A-7C and Tables 4). Moreover, IFN-γ production was also enhanced comparing to IL-2 alone and IL-2+IL-12 (FIG. 9). However, the killing activity and the antigen presenting cell (APC) activity in IL-2+IL-12+IL-18 groups did not have significant difference comparing to IL-2+IL-12 (FIGS. 5, 8, 10).

TABLE 3

|  | Fold change* |
| --- | --- |
| IL-2 | 11.11X |
| IL-2 + IL-12 | 7.06X |
| IL-2 + IL-12 + IL-18 15 ng/ml | 2.91X |
| IL-2 + IL-12 + IL-18 45 ng/ml | 2.81X |
| IL-2 + IL-12 + IL-18 135 ng/ml | 2.64X |

* The "Fold change" was calculated by the cell number on day 15/the cell number on day 0.

TABLE 4

Net MFI# of surface markers in cells treated with IL-2, IL-12 and IL-18 on day 12

|  | CD3 | TCR γ9 | TCR δ2 | CD69 | CD11c | CXCR4 | CXCR3 | IFN-γ |
| --- | --- | --- | --- | --- | --- | --- | --- | --- |
| IL-2 | 2.53 | 30.03 | 38.14 | 0.08 | 0.09 | 1.34 | 2.6 | −0.25 |
| IL-2 + IL-12 | 6.1 | 25.22 | 38.32 | 0.43 | 4.38 | 3.64 | 0.2 | 0.47 |
| IL-2 + IL-12 + IL-18 15 ng/ml | 3.22 | 18.95 | 22.29 | 0.58 | 2.37 | 3.62 | 0.79 | 3.35 |
| IL-2 + IL-12 + IL-18 45 ng/ml | 4.24 | 17.86 | 24.83 | 0.74 | 1.00 | 4.99 | 0.96 | 3.82 |
| IL-2 + IL-12 + IL-18 135 ng/ml | 4.24 | 17.07 | 23.23 | 0.8 | 2.47 | 4.81 | 0.94 | 3.8 |

Net MFI was calculated by (sample MFI - isotype/unstained MFI).

As a result, in view of the cell yield results, the addition of IL-18 on day 12 provides additional effects on the IFN-γ production and cell marker expression. However, it seems no difference or even better of the killing activity and the APC activity in IL-2+IL-12+IL-18 group than IL-2+IL-12 group.

Example 3: Preparation of Initial Cell 40 mL of peripheral blood was collected from a healthy volunteer into vacuum tubes containing K2EDTA. The blood sample was mixed with equal volume of pre-warmed phosphate-buffered saline (PBS) (Biological Industries, Israel). The 40 mL diluted peripheral blood aliquot was placed into a 50 mL centrifuge tube and loaded 10 mL pre-warmed Ficoll-Paque™ PREMIUM. The centrifuge tube was centrifuged at 930×g, in room temperature for 30 min. The mononuclear cells in the interface layer were collected and washed once in PBS. The mononuclear cells were cultured with AIM-V in the presence of human platelet lysate and cytokine cocktails.

Example 4: Modified T Cell Culture

The mononuclear cells from Example 3 were cultured as follows:
(a) Contacting $1\times10^6$/mL mononuclear cells with an inducing culturing medium comprising AIM-V medium, HPL (concentration: 2% v/v), IL-2 (concentration: 60 ng/mL) and zoledronic acid (concentration: 5 μM) on day 0.
(b) Replacing the inducing culturing medium with a first culturing medium comprising AIM-V medium, HPL (concentration: 4% v/v) and IL-2 (concentration: 120 ng/mL) on day 3, and harvesting and spinning down half of the cells, followed by re-suspending cell pellet into $2\times10^6$/mL cells with a first culturing medium comprising AIM-V medium, HPL and IL-2 on day 6.
(c) Harvesting and spinning down half of the cells in step (b), followed by re-suspending cell pellet into $2\times10^6$/mL cells with a second culturing medium comprising AIM-V medium, HPL (concentration: 4% v/v), IL-2 (concentration: 120 ng/mL) and IL-12 (concentration: 2 ng/mL) on day 9 and 12.
(d) Collecting all of the cultured cells in step (c) on day 15.

Optionally, the culturing medium for culturing the cells may be replaced with a fresh medium, with the same constituents on day 3 and day 12. For example, the initial cell may be cultured as follows:
(a) Contacting $1\times10^6$/mL mononuclear cells with an inducing culturing medium comprising AIM-V medium, HPL (concentration: 2% v/v), IL-2 (concentration: 60 ng/mL) and zoledronic acid (concentration: 5 μM) on day 0.
(b) Harvesting and spinning down half of the cells in step (a), followed by re-suspending cell pellet into $2\times10^6$/mL cells with a first culturing medium comprising AIM-V medium, HPL (concentration: 4% v/v) and IL-2 (concentration: 120 ng/mL) on day 3.
(c) Replacing a medium with the first culturing medium comprising AIM-V medium, HPL and IL-2 on day 6.
(d) Harvesting and spinning down half of the cells in step (c), followed by re-suspending cell pellet into $2\times10^6$/mL cells with a second culturing medium comprising AIM-V medium, HPL (concentration: 4% v/v), IL-2 (concentration: 120 ng/mL) and IL-12 (concentration: 2 ng/mL) on day 9.
(e) Replacing a medium with the first culturing medium comprising AIM-V medium, HPL, IL-2 and IL-12 on day 12.
(f) Collecting all of the cultured cells in step (e) on day 15.

Alternatively, the second culturing medium may be changed to a third culturing medium on day 12. For example, the initial cell may be cultured as follows:
(a) Contacting $1\times10^6$/mL mononuclear cells with an inducing culturing medium comprising AIM-V medium, HPL (concentration: 2% v/v), IL-2 (concentration: 60 ng/mL) and zoledronic acid (concentration: 5 μM) on day 0.
(b) Harvesting and spinning down half of the cells in step (a), followed by re-suspending cell pellet into $2\times10^6$/mL cells with a first culturing medium comprising AIM-V medium, HPL (concentration: 4% v/v) and IL-2 (concentration: 120 ng/mL) on day 3 and 6.
(c) Harvesting and spinning down half of the cells in step (b), followed by re-suspending cell pellet into $2\times10^6$/mL cells with a second culturing medium comprising AIM-V medium, HPL (concentration: 4% v/v), IL-2 (concentration: 120 ng/mL) and IL-12 (concentration: 2 ng/mL) on day 9.
(d) Harvesting and spinning down half of the cells in step (c), followed by re-suspending cell pellet into $2\times10^6$/mL cells with a third culturing medium comprising AIM-V medium, HPL (concentration: 4% v/v), IL-2 (concentration: 120 ng/mL), IL-12 (concentration: 2 ng/mL) and IL-18 (concentration: 45 ng/mL) on day 12.
(e) Collecting all of the cultured cells in step (d) on day 15.

The cultured cells in step (e) of the previous paragraph were assayed for their phenotype using Navios Flow Cytometer (10 COLORS/3 LASERS, serial number: AW40325, Beckman Coulter, Inc. USA), Kazula software version 2.1 (Beckman Coulter, Inc. USA) and antibodies listed in Table 5.

In an embodiment, on day 3, day 6, day 9, or day 12, the cells can be subcultured with new medium. In another embodiment, on day 3, day 6, day 9, or day 12, the cells are not subcultured. Instead, the medium are replaced with fresh medium as indicated.

TABLE 5

Reagents used for cultivation functional assay and phenotyping of the modified T cells

| Name | Cat. # | Vender |
|---|---|---|
| Cultivation | | |
| Phosphate-Buffered Saline, 1X without $Ca^{2+}$ and $Mg^{2+}$ | 21-040-CV | Corning |
| CTS ™ AIM V Serum Free Medium | 0870112DK | Gibco |
| GMP UltraGRO-Advanced | HPCFDCGL05 | AventaCell |
| Ficoll-paque Premium 1.077 | 17-5442-03 | GE Healthcare |
| R&D GMP, Human, IL-2 | 202-GMP-050 | R&D |
| Miltenyi Biotec, Human, IL-12 | 170-076-174 | Miltenyi biotec |
| Human, IL-18, 100ug | 592106 | BioLegend |
| Bonecare | 4110005205220 | Nang Kuang |
| Functional assay | | |
| CTS ™ AIM V Serum Free Medium | 0870112DK | Gibco |
| GMP UltraGRO-Advanced | HPCFDCGL05 | AventaCell |
| Human, IL-2 | 589108 | BioLegend |

TABLE 5-continued

Reagents used for cultivation functional assay and phenotyping of the modified T cells

| Name | Cat. # | Vender |
|---|---|---|
| Human, IL-15, 500 μg | 570308 | BioLegend |
| Killing assay Kit (PanToxiLux ™) | PTL8028 | OncoImmunin |
| CellTrace ™ Violet Cell Proliferation Kit | C34557 | Invitrogen |
| LEAF ™ Purified-anti human CD3 | 317304 | Biolegend |
| LEAF ™ Purified anti-human CD28 | 302914 | BioLegend |
| CD3-ECD | A07748 | Beckman Coulter |
| CD8-APC-Alexa Fluor 700 | A66332 | Beckman Coulter |
| Phenotype | | |
| CD3 FITC | 300406 | BioLegend |
| TCR Vδ2 PE | 331408 | BioLegend |
| CD11c-PE | 301606 | BioLegend |
| Mouse IgG1, κ Isotype Ctrl-PE | 400112 | BioLegend |
| IFN-g PerCp/Cy5.5 | 502526 | Biolegend |
| Mouse IgG1-PerCP/Cy5.5 | 400150 | Biolegend |
| TCR Vγ9-APC | 331310 | BioLegend |
| CD69-Pacific Blue | 310919 | BioLegend |
| CD183 (CXCR3)-Pacific Blue | 353724 | BioLegend |
| mouse IgG1, κ Isotype Ctrl-Pacific Blue | 400131 | BioLegend |
| CD184 (CXCR4)-BV510 | 306536 | BioLegend |
| Mouse IgG2a, κ Isotype Ctrl-BV510 | 400268 | BioLegend |
| CD3-Krome orange | B00068 | Beckman Coulter |

Results: As shown in FIGS. 3 and 7, the obtained modified T cells have the T and DC related phenotypes of $CD3^{Hi}TCR\ \gamma9^{Hi}TCR\ \delta2^{Hi}CD69^{Dim}CD11c^{Hi}CXCR4^{Hi}CXCR3^{Dim}$.

Example 5: Determination of the Functionality of T Cells

"Killing" Assay

Evaluation of cytotoxicity of the modified T cells from Example 4 was performed by PanToxilux kit (OncoImmunin, Inc.). Human chronic myelogenous leukemia (CML) cell line, K562, served as a target cell and stained with TFL4 under the optimal concentration for 50 minutes. Co-incubation of TFL4 labeled target cell and the modified T cells with the caspase substrate under 37° C. for 20 minutes. The cells were harvested and analyzed the signal of TFL4⁺substrate⁺ via flow cytometry. A positive cells for caspase is indicative of killing.

Results: As shown in FIGS. 5 and 8, the percentage of caspase positive target cells (without modified T cells) was 0.60%, whereas the percentage of caspase positive target cells (with modified T cells) was more than 25% in the groups of IL-2+IL-12 and IL-2+IL-12+various doses of IL-18. This result shows the modified T cells in the present disclosure has a cytotoxic effect on the leukemia target cells K562 and the effect was enhanced comparing to the IL-2 only group.

Assay of Antigen-Presenting Activity

Evaluation of the activity of antigen-presentation of the modified T cells from Example 4 was performed by mixed lymphocyte reaction (MLR). Responder cells (CD25⁻ PBMCs) were enriched and stained with CellTrace™ Violet cell proliferation kit (Invitrogen). Co-culture of CellTrace Violet-labeled CD25 PBMCs and the modified T cells under 37° C. for 5 days. hIL-2 and hIL-15 were added on day 1 and day 3 to reduce the threshold of TCR engagement. The cells were then harvested and analyzed the CellTrace Violet-diluted pattern via flow cytometry.

Results: As shown in FIG. 10, 14.44% of the responder cells in the IL-2 only group were dividing as identified by flow cytometry. However, more than 28.56% of the cells were dividing in the presence of the modified T cells from Example 4. This result shows the modified T cells has an antigen-presentation activity on the CD25⁻ PBMCs responder cells.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method of culturing a modified T cell, comprising obtaining a body fluid comprising mononuclear cells, wherein the mononuclear cells comprise T cells;
   contacting the mononuclear cells with an inducing culturing medium comprising IL-2 and zoledronic acid to obtain a first cultured cell population;
   contacting the first cultured cell population with a first culturing medium comprising IL-2 to obtain a second cultured cell population;
   contacting the second cultured cell population with a second culturing medium comprising IL-2 and IL-12 to obtain a third cultured cell population; and
   contacting the third cultured cell population with a third culturing medium comprising IL-2, IL-12 and IL-18 after contacting with the second culturing medium to obtain a fourth cultured cell population that comprises the modified T cells;
   wherein each of the inducing culturing medium, the first culturing medium, the second culturing medium, and the third culturing medium further comprises L-glutamine, streptomycin sulfate, gentamicin sulfate and human platelet lysate.

2. The method of claim 1, wherein the mononuclear cells are derived from peripheral blood, cord blood or bone marrow.

3. The method of claim 1, wherein the mononuclear cells are in contact with the inducing culturing medium for about 1-3 day(s).

4. The method of claim 1, wherein the first cultured cell population is in contact with the first culturing medium for about 1-6 day(s).

5. The method of claim 1, wherein the second cultured cell population is in contact with the second culturing medium for about 1-3 day(s).

6. The method of claim 1, wherein the third cultured cell population is in contact with the third culturing medium for about 1-3 day(s).

7. The method of claim 1, further comprising isolating a modified T cell with a phenotype of $CD3^{Hi}TCR\ \gamma9^{Hi}TCR\ \delta2^{Hi}CXCR4^{Hi}$.

8. The method of claim 7, wherein the modified T cell further comprises a phenotype of $CD69^{Dim}CD11c^{Hi}CXCR3^{Dim}$.

9. The method of claim 7, wherein the modified T cell further comprises a phenotype of IFN-$\gamma^{Hi}$.

* * * * *